United States Patent
Ben-Neriah et al.

(10) Patent No.: US 6,905,836 B2
(45) Date of Patent: Jun. 14, 2005

(54) METHODS FOR IDENTIFYING COMPOUNDS THAT INHIBIT UBIQUITIN-MEDIATED PROTEOLYSIS OF IκB

(75) Inventors: Yinon Ben-Neriah, Mevasseret Zion (IL); Irit Alkalay-Snir, Zur Hadassah (IL); Ada Hatzubai, Kibutz Tzuba (IL); Etti Ben Shushan, Akiva (IL); Matti Davis, Modiin (IL); Avraham Yaron, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/361,394

(22) Filed: Feb. 10, 2003

(65) Prior Publication Data

US 2004/0014026 A1 Jan. 22, 2004

Related U.S. Application Data

(63) Continuation of application No. PCT/IB01/02428, filed on Aug. 10, 2001.

(30) Foreign Application Priority Data

Aug. 11, 2000 (EP) ............................................. 00117429

(51) Int. Cl.⁷ ............................ C12Q 1/50; C12Q 1/48; C12Q 1/66; C12N 15/09
(52) U.S. Cl. .............................. 435/17; 435/15; 435/8; 435/69.2; 435/69.1; 530/300
(58) Field of Search .............................. 435/17, 15, 8, 435/69.2, 69.1; 530/300

(56) References Cited

U.S. PATENT DOCUMENTS 6,232,081 B1 * 5/2001 Harper et al. ................ 435/7.1

2004/0014026 A1 * 1/2004 Ben-Neriah et al. ........... 435/4

FOREIGN PATENT DOCUMENTS

| EP | 1182251 A1 * | 2/2002 | ............ C12N/9/00 |
|---|---|---|---|
| WO | WO 94/12666 | 6/1994 | |
| WO | WO 99/38969 | 8/1999 | |
| WO | WO 00/34447 | 6/2000 | |

OTHER PUBLICATIONS

Jordan, Peter et al., "Major Cell Surface-Located Protein Substrates of an Ecto-Protein Kinase are Homologs of Known Nuclear Proteins", Biochemistry, vol. 33, No. 49, 1994, pp. 14696–14706; XP002162187.

Yaron et al., "Identification of the Receptor Component of the IkBα–Ubiquitin Ligase", Nature, GB, MacMillan Journals, London, vol. 396, No. 6711, Dec. 10, 1998, pp. 590–594; XP002101957.

Hatakeyama, E. A., "Ubiquitin–Dependent Degradation of IkBα is Mediated by a Ubiquitin Ligase Skpl/Cul 1/F–Box Protein FWDI", Proceedings of the National Academy of Sciences (US), vol. 96, Mar. 1999, pp. 3859–3863; XP002152297.

(Continued)

*Primary Examiner*—Louise N. Leary
(74) *Attorney, Agent, or Firm*—Frommer Lawrence & Haug LLP; William S. Frommer

(57) ABSTRACT

Compounds that inhibit ubiquitin-mediated proteolysis of phosphorylated IκB by interfering, directly or indirectly, with the ability of β-TrCP/E3RS to engage in protein-protein association involving hnRNP-U, are useful as drugs for treating conditions associated with NF-κB activation. Cellular and non-cellular screening methods for identifying such compounds are based on monitoring the association/dissociation of β-TrCP/E3RS.

54 Claims, 16 Drawing Sheets

OTHER PUBLICATIONS

Kiledjian, M. et al., "Primary Structure and Binding Activity of the hnRNP U Protein: Binding RNA Through RGG Box", EMBO J., vol. 11, No. 7, 1997, pp. 2655–2664; XP001108945.

Alkalay, I. et al., (1995) *Proc Natl Acad Sci U S A* 92, 10599–603.

Dreyfuss, G., Choi, Y. D., and Adam, S. A. (1984). Characterization of heterogeneous nuclear RNA–protein complexes in vivo with monoclonal antibodies. Mol Cell Biol 4, 1104–14.

Hatakeyama, S., Kitagawa, M., Nakayama, K., Shirane, M., Matsumoto, M., Hattori, K., Higashi, H., Nakano, H., Okumura, K., Onoe, K., Good, R. A., and Nakayama, K. (1999). Ubiquitin–dependent degradation of IkBα is mediated by a ubiquitin ligase Skp1/Cul 1/F–box protein FWDI. Proc Natl Acad Sci U S A 96, 3859–63.

Kiledjian, M., and Dreyfuss, G. (1992). Primary structure and binding activity of the hnRNP U protein: binding RNA through RGG box. Embo J 11, 2655–64.

Margottin, F., Bour, S. P., Durand, H., Selig, L., Benichou, S., Richard, V., Thomas, D., Strebel, K., and Benarous, R. (1998). A novel human WD protein, h–beta TrCP, that interacts with HIV-1 Vpu connects CD4 to the ER degradation pathway through an F–box motif. Mol Cell 1, 565–574.

Pinol–Roma, S., Choi, Y. D., Matunis, M. J., and Dreyfuss, G. (1988). Immunopurification of heterogeneous nuclear ribonucleoprotein particles reveals an assortment of RNA–binding proteins. Genes Dev 2, 215–27.

Romig, H., Fackelmayer, F. O., Renz, A., Ramsperger, U., and Richter, A. (1992). Characterization of SAF–A, a novel nuclear DNA binding protein from HeLa cells with high affinity for nuclear matrix/scaffold attachment DNA elements. Embo J 11, 3431–40.

Suzuki, H., Chiba, T., Suzuki, T., Fujita, T., Ikenoue, T., Omata, M., Furuichi, K., Shikama, H., and Tanaka, K. (2000). Homodimer of two F–box proteins β–TrCP1 or β–TrCP2 binds to IkBα for signal–dependent ubiquitination. J Biol Chem 275, 2877–84.

Winston, J. T., Strack, P.., Beer–Romero, P., Chu, C. Y., Elledge, S. J., and Harper, J. W. (1999). The SCF b–TRCP–ubiquitin ligase complex associates specifically with phosphorylated destruction motifs in IkBa and b–catenin and stimulates IkBa ubiquitination in vitro. Genes Dev 13, 270–283.

Yaron, A., Gonen, H., Alkalay, I., Hatzubai, A., Jung, S., Beyth, S., Mercurio, F., Manning, A. M., Ciechanover, A., and Ben–Neriah, Y. (1997). Inhibition of NF–kB cellular function via specific targeting of the IkB–ubiquitin ligase. EMBO J16, 6486–6494.

Yaron, A., Hatzubai, A., Davis, M., Lavon, I., Amit, S., Manning, A. M., Andersen, J. S., Mann, M., Mercurio, F., and Ben–Neriah, Y. (1998). Identification of the receptor component of the IkBa–ubiquitin ligase. Nature 396, 590–594.

\* cited by examiner

Fig. 2B,C
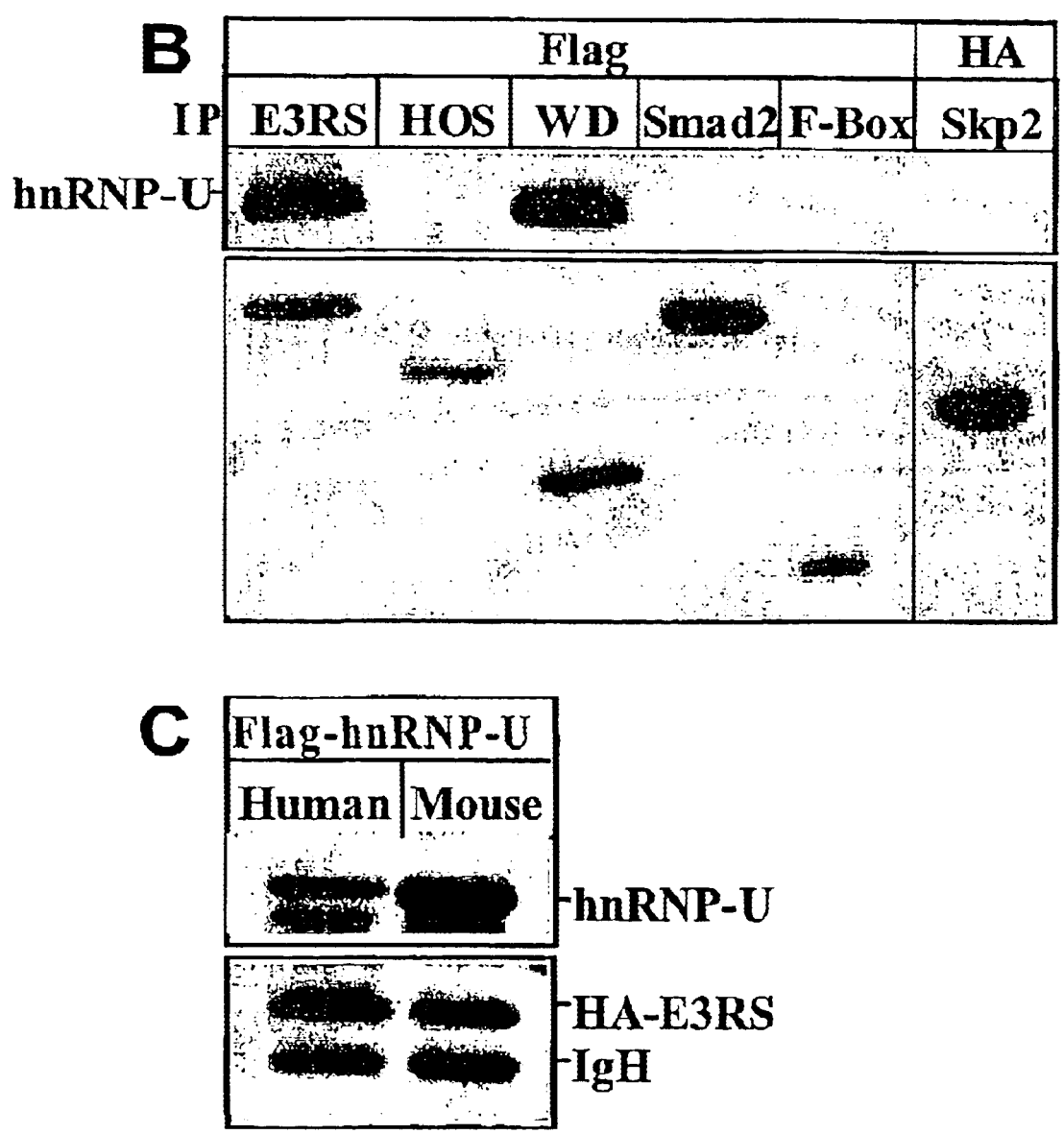

Fig. 3B,C
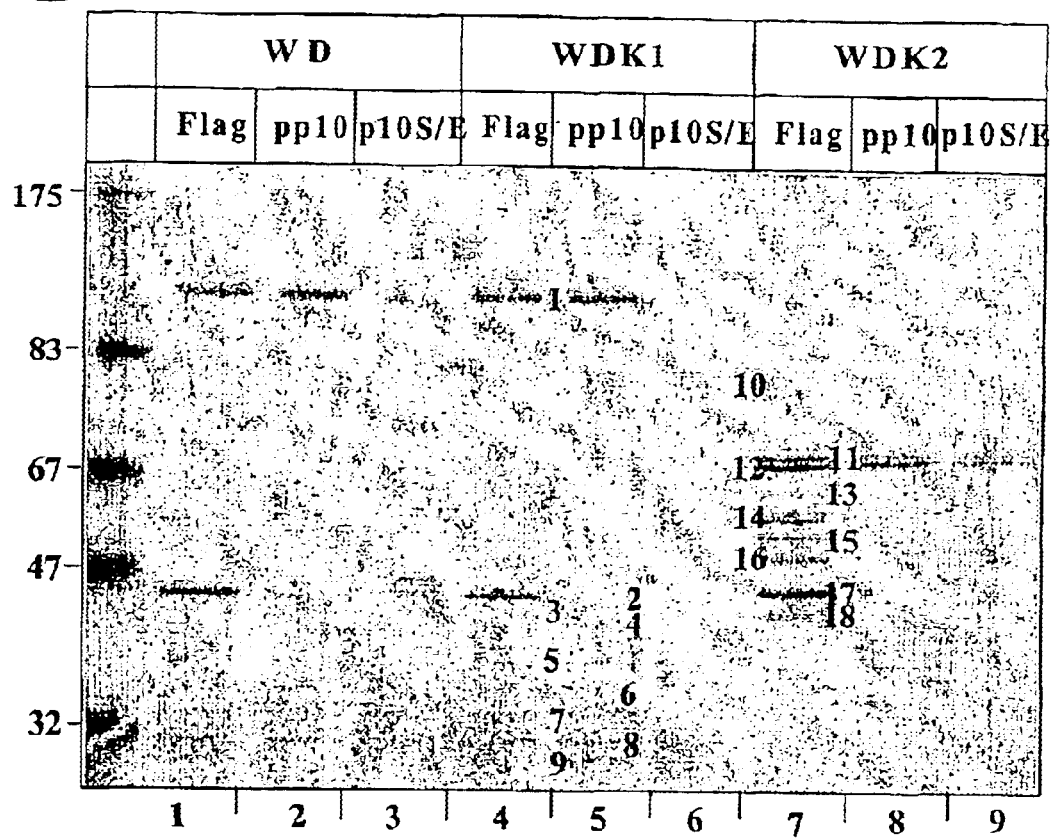
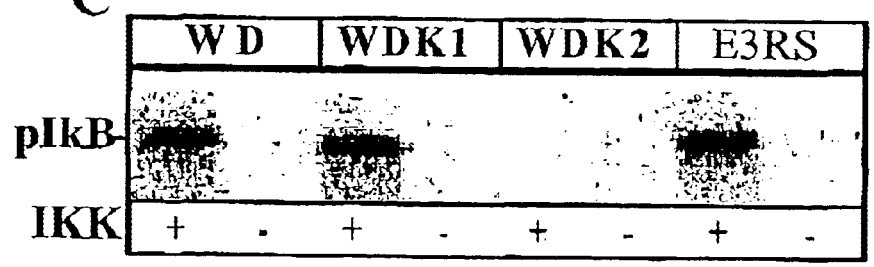

Fig. 4C,D
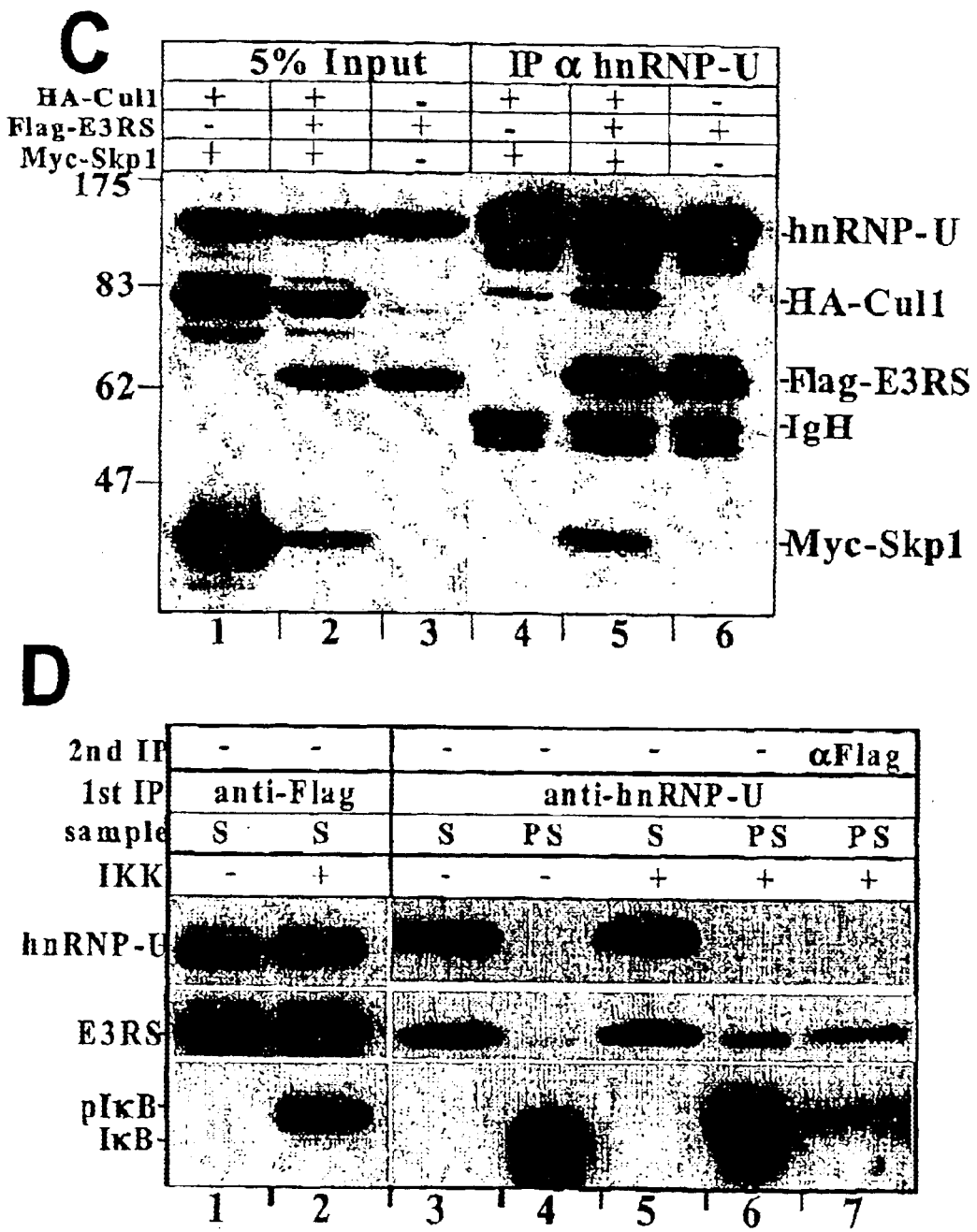

Fig. 6/1
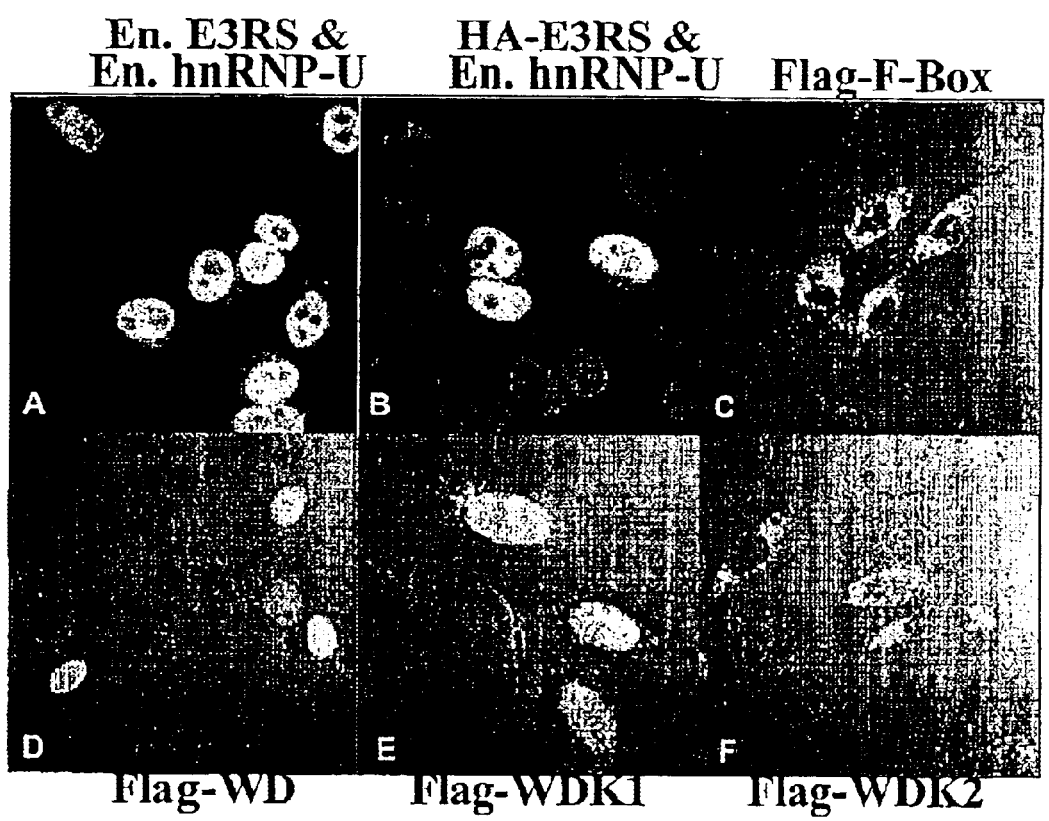

Fig. 6/2

Fig. 8
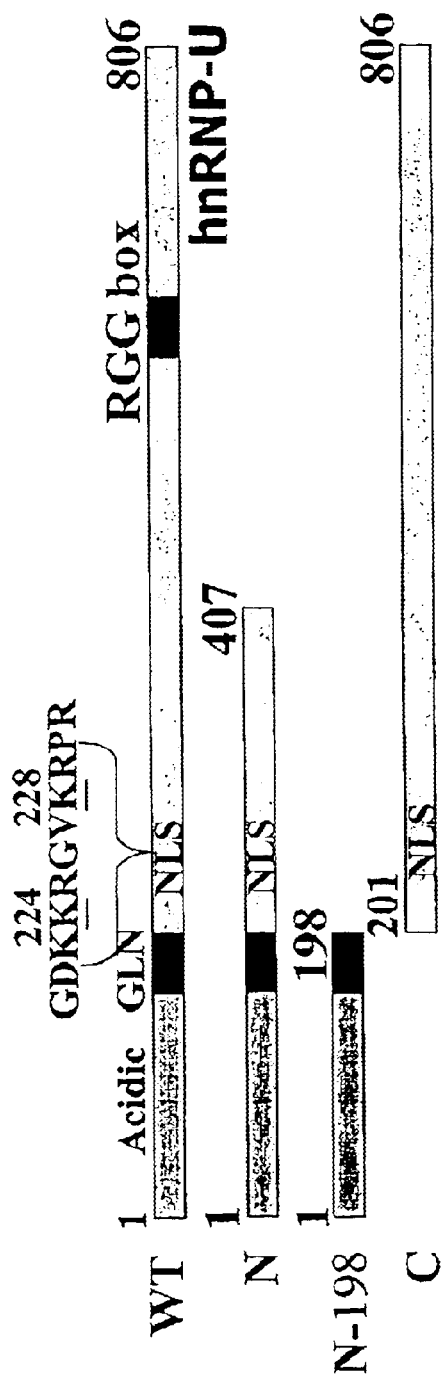
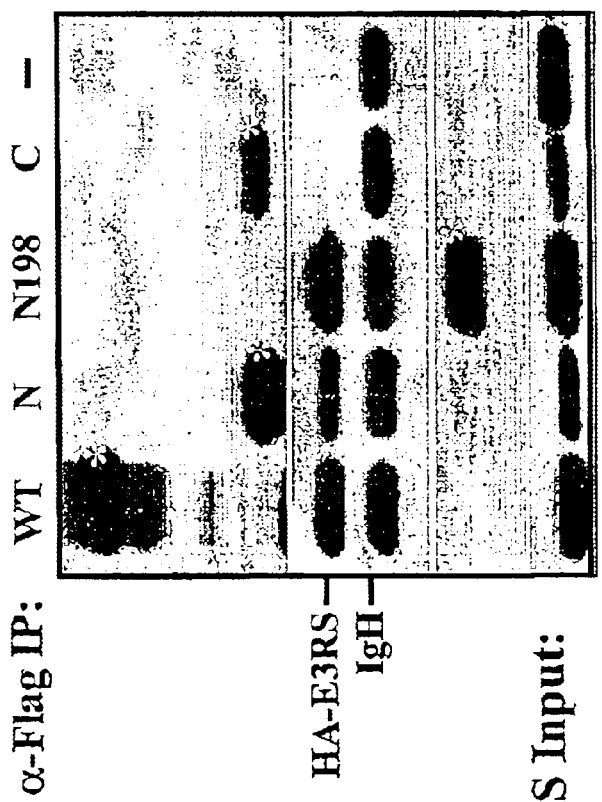

SEQUENCE LISTING

<160> NUMBER OF SEQ ID NOS: 7

<210> SEQ ID NO 1
<211> LENGTH: 14
<212> TYPE: PRT
<213> ORGANISM: Homo sapiens

<400> SEQUENCE: 1

Glu Asp Glu Asn Gly Asp Asp Gln Gly Phe Gln Glu Gly Glu
 1               5                   10

<210> SEQ ID NO 2
<211> LENGTH: 13
<212> TYPE: PRT

-continued

```
<213> ORGANISM: Homo sapiens

<400> SEQUENCE: 2

Asp Glu Leu Gly Asp Glu Glu Gly Ala Gly Asp Glu
 1               5                  10

<210> SEQ ID NO 3
<211> LENGTH: 12
<212> TYPE: PRT
<213> ORGANISM: Homo sapiens

<400> SEQUENCE: 3

Leu Asp Gly Asp Gln Met Glu Leu Gly Glu Glu Asn
 1               5                  10

<210> SEQ ID NO 4
<211> LENGTH: 22
<212> TYPE: PRT
<213> ORGANISM: Homo sapiens

<400> SEQUENCE: 4

Gly Ile Ser Ala Leu Asp Gly Asp Gln Met Glu Leu Gly Glu Glu Asn
 1               5                  10                  15

Gly Ala Ala Gly Ala Ala
            20

<210> SEQ ID NO 5
<211> LENGTH: 19
<212> TYPE: PRT
<213> ORGANISM: Homo sapiens

<400> SEQUENCE: 5

Lys Ala Leu Lys Phe Met Asn Ser Ser Glu Arg Glu Asp Cys Asn Asn
 1               5                  10                  15

Gly Glu Pro

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
tagcggccgc aatgagttcc tcgcctgtt                                        29

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
tagcggccgc tcaataatat ccttggtgat a                                     31
```

METHODS FOR IDENTIFYING COMPOUNDS THAT INHIBIT UBIQUITIN-MEDIATED PROTEOLYSIS OF IκB

This application is a continuation of PCT/IB01/02428 filed Aug. 10, 2001.

The present invention relates generally to methods for modulating, in particular inhibiting, the activation of nuclear factor kappaB (NF-κB). The invention is more particularly related to methods for identifying compounds that modulate ubiquitination of phosphorylated IκBα.

NF-κB is a transcription factor that plays a pivotal role in the highly specific pattern of gene expression observed for immune, inflammatory and acute phase response genes, including interleukin 1, interleukin 8, tumor necrosis factor and certain cell adhesion molecules. Like other members of the Rel family of transcriptional activators, NF-κB is sequestered in an inactive form in the cytoplasm of most cell types.

Important modulators of NF-κB activation are the inhibitor proteins IκBα, IκBε and IκBβ (referred to herein as IκB), which associate with (and thereby inactivate) NF-κB in vivo. Activation and nuclear translocation of NF-κB occurs following signal-induced phosphorylation of IκB, which leads to proteolysis via the ubiquitin pathway. In response to a stimulus, the NF-κB-associated IκB is phosphorylated, rendering it a target for degradation and thereby releasing and activating NF-κB. A variety of extra-cellular stimuli including mitogens, cytokines, antigens, stress inducing agents, UV light and viral proteins initiate a signal transduction pathway that ultimately leads to NF-κB release and activation.

IκB degradation via the ubiquitin pathway has been suggested as a target mechanism for interfering with the activation of NF-κB.

U.S. Pat. No. 5,932,425 (WO 98/36070) describes a method for identifying agents that modulate the ubiquitination of phosphorylated of IκBα and/or IκBβ. The method comprises incubating IκB with a cellular extract to allow phosphorylation of IκB and formation of a complex and assaying the ability of a test substance to modulate the ubiquitination of the formed complex.

The method for identifying modulators of NF-κB activity described in WO 00/34447 relies on comparing the ability of an E3 (a ubiquitin ligase), to enhance ubiquitination of phosphorylated IκB in the presence and absence of a test compound. This method requires the use of IκB, phosphorylated by IKK.

U.S. Pat. No. 6,600,262 describes an alternative method for identifying compounds which modulate the ubiquitin-mediated proteolysis of a IκB polypeptide, which is based on determining the ability of a compound to modulate the ubiquitination of IκB by the HECT E3. However, no HECT ligase has yet been implicated in the signal-induced degradation of IκB.

Ubiquitin-mediated protein degradation is a highly selective process that is achieved through the concerted action of a versatile set of enzymes (Hershko and Ciechanover, 1998; Varshavsky, 1997). A single E1 enzyme (ubiquitin activating enzyme) is responsible for activation of the small protein ubiquitin, which is then passed on via trans-acetylation to several E2 enzymes (ubiquitin conjugating enzyme). Each E2 may collaborate with several different E3 proteins in creating a protein-ubiquitin conjugate. The E3s, referred to as ubiquitin-protein ligases, confer specificity to the system and share a common property: substrate recognition and binding. Whereas the E2 proteins bear a significant homology to each other, the E3s, many of which are associated with large multisubunit complexes, form a highly heterogeneous group. Within these complexes the specific task of individual subunits is not always clear (Yamano et al., 1998; Zachariae and Nasmyth, 1999). Moreover, the composition of the complex is not necessarily static and may be subject to regulatory processes associated with the functional status of the cell (Fang et al., 1998; Zachariae et al., 1998). Only a few E3s have been characterized in detail and there is only scant information regarding mammalian E3s. Among the latter, one of the better-defined E3s is $SCF^{\beta-TrCP/E3RS}$, a recently identified E3 complex that targets pIκBα and β-catenin for degradation (reviewed in (Karin and Ben-Neriah, 2000; Maniatis, 1999; Polakis, 1999)). SCF-type E3s are assemblies of several common (Skp1, Cul1 and Roc1/Rbx1/Hrt1) and single variable (F-box protein) protein components, which were discovered and have mainly been characterized in yeast (Deshaies, 1999; Patton et al., 1998). Genes encoding certain SCF subunits are essential to cell cycle progression and mutations in the different subunits result in a similar phenotype of cell cycle arrest, supporting the view that they are acting in concert. Many substrates of these E3s have a common feature, phosphorylation as a prerequisite for being recognized by the ligase. Having no apparent catalytic function of their own, SCF ligases rely on E2s for facilitating the covalent attachment of ubiquitin to the substrate. With the exception of the variable F-box proteins, the function of other SCF subunits is only partially resolved (Deshaies, 1999). At least one subunit, Skp1, is thought to serve as an adapter that links the F-box protein to the rest of the complex. The other subunits, Cul1 and the newly discovered subunit ROC1/Rbx1/Hrt1, may function in recruiting an E2 onto the substrate through a motif called the R-box (a RING finger, small metal-binding domain), and are involved in the polymerization of the ubiquitin chain (Ohta et al., 1999; Seol et al., 1999; Skowyra et al., 1999; Tan et al., 1999). Polyubiquitination is a signal for engaging the 26S proteasome and targeting substrates for rapid degradation. Although there has been rapid progress in the biochemical characterization of the SCF-type ligases, many aspects of their function remain mostly obscure, particularly the developmental and cellular regulation of SCF complexes in multicellular organisms.

There is a need for an improved understanding of IκB degradation in order to provide a basis for interfering with this process and thus with the activation of NF-κB.

Thus, it was an object of the invention to elucidate the regulatory process of IκBα degradation via the ubiquitin pathway involving SCF-type IκBα-E3 and to identify modulators of this degradation process in order to use such modulators for treating diseases associated with the activation of NF-κB.

To this end, an analysis was conducted in the experiments of the present invention, which was prompted by the surprising observation that β-TrCP/E3RS (the E3 receptor subunit, in the following also termed "E3RS"), resides predominantly in the nucleus. This phenomenon has been observed in different cell types and is also apparent in some recently published reports by other groups (Sadot et al., 2000; Winston et al., 1999). Being a component of a SCF complex, E3RS, which is itself devoid of a nuclear localization signal, could be led to the nucleus by an associated SCF component, such as the NLS containing Cul1. However, it appears that the distribution of Cul1 in the cell is quite distinct from that of the endogenous E3RS (FIG. 1). Furthermore, only a small fraction of an exogenously-expressed E3RS is associated with endogenous Skp1 and Cul1, whereas nearly all of the overexpressed E3RS is nuclear. Therefore, the known SCF partners are unlikely to be responsible for the accumulation of E3RS in the nucleus.

In the experiments of the present invention, hnRNP-U has been identified as the dedicated chaperone of E3RS (Yaron et al., 1998), the receptor component of the IκB-E3.

hnRNP-U was discovered as an hnRNP (Dreyfuss et al., 1984) and cloned (Kiledjian and Dreyfuss, 1992). It is an abundant protein, which similarly to many other hnRNPs, may participate in the maintenance of the internal nuclear architecture (Gohring et al., 1997). It adheres to the nuclear scaffold at A/T-rich regions through a specific DNA binding domain (therefore, also termed Scaffold Attachment Factor-A) and binds RNA through a separate domain, the RGG box (Kiledjian and Dreyfuss, 1992). hnRNPs represent a diverse group of proteins containing RNA-binding motifs, which participate in multiple regulatory processes that involve RNA and RNPs. Among the latter is mRNA splicing and transport, transcription and DNA recombination, the maintenance of telomere length and the control of RNA stability (Krecic and Swanson, 1999). Many of the 20 major hnRNP proteins shuttle in and out of the nucleus, yet are predominantly nuclear, possibly due to the presence of nuclear retention signals (Nakielny and Dreyfuss, 1999). Although several shuttling hnRNPs are involved in mRNA export, none have been implicated in protein transport in or out of the nucleus. Thus, the biological function of hnRNP-U has not been resolved (Krecic and Swanson, 1999). It has been found in the present invention that hnRNP-U interacts selectively with the WD repeat domain of E3RS, a feature indicated by its failure to associate with its most closely related F-box protein β-TrCP2/HOS. This selectivity is striking since β-TrCP2/HOS displays 85% overall similarity to E3RS and 93% identity throughout the WD40 repeat domain. Another mammalian F-box protein, Skp2, which contains a leucine-rich interaction domain, rather than the WD domain (Krek, 1998), is also incapable of associating with hnRNP-U. Therefore, hnRNP-U is not a common component of the SCF-type E3 complex. Unless engaged with a substrate, E3RS is stoichiometrically associated with hnRNP-U, an interaction that is supported by prior association of β-TrCP/E3RS with Skp1. Hence, the cellular IκB-E3 is composed of a ternary complex of β-TrCP/E3RS/Skp1/hnRNP-U alone or in association with other components of the SCF complex (Cul1 and Roc1) (Deshaies, 1999). In the presence of pIκBα, hnRNP-U dissociates from the complex, allowing the binding and ubiquitination of the substrate. A specific mutation in WD domain of E3RS (K326A) abrogates both hnRNP-U and pIκBα binding, indicating that the interaction site of E3RS with the two proteins is identical or overlapping.

In summary, the experiments of the invention have shown that the ubiquitination of pIκBα takes place both in the cytoplasm and in the nucleus, ensuring maximal activation of NF-κB. hnRNP-U was shown to have a chaperone function and to be essential for transporting the IκBα-E3 into the nucleus. It was shown that a mutant β-TrCP/E3RS, which is incapable of associating with hnRNP-U, cannot be transported into the nucleus.

Thus, the present invention is based on the finding that maintenance of the functional competence and subcellular distribution of both the subunit β-TrCP/E3RS and the entire E3 complex (the SCF$^{β-TrCP/E3RS}$) depend on the interaction hnRNP-U with E3RS and that any interference with this interaction would abrogate the function of the E3.

The present invention provides screening methods for identifying agents that modulate, in particular inhibit, the ability of β-TrCP/E3RS to engage in protein-protein association with hnRNP-U, thus compromising IκBα-E3 activation and, consequently, NF-κB activation.

These compounds (in the following termed "E3RS inhibitors") have the potential of being used as drugs or being developed into drugs for the treatment of disorders associated with NF-κB activation. These NF-κB inhibitors are distinct from proteasome inhibitors, which also affect pIκBα degradation, yet have pleiotropic effects in many other cellular pathways, e.g. the cell cycle.

Accordingly, in a first aspect, the invention relates to a method for identifying a compound that modulates, in particular inhibits, ubiquitin-mediated proteolysis of phosphorylated IκB, wherein the compound is tested for its capacity to directly or indirectly modulate, in particular compete for or interfere with, the ability of β-TrCP/E3RS to engage in protein-protein association with hnRNP-U.

The compounds may inhibit the association of β-TrCP/E3RS and hnRNP-U by interfering with the interaction of the proteins. This may be caused by preventing the association of the proteins or by inducing dissociation of the hnRNP-U/E3RS complex.

By way of example, a compound may exert its inhibitory effect by competing with either hn-RNP-U or β-TrCP/E3RS for interacting with its partner. Alternatively, the compound may prevent the association of β-TrCP/E3RS with hnRNP-U by modifying one of the proteins in a manner that prevents its interaction with its partner.

In the following, the term "interfering with the interaction of the proteins" is used synonymously with the term "disrupting the complex".

Another mechanism by which the compound may exert its inhibitory effect is an indirect one, i.e. by compromising the ability of another protein, e.g. Skp1, to stabilize the interaction of β-TrCP/E3RS and hnRNP-U. A compound's ability to affect the interaction of β-TrCP/E3RS and hnRNP-U indirectly by inhibiting Skp1 may be due to affecting E3RS-Skp1 interaction or inhibiting the Skp1 protein per se.

In a first embodiment, the screening method of the invention is based on a non-cellular biochemical assay.

In this method, by way of example, a complex containing the interacting proteins hnRNP-U and E3RS, or the protein domains required for binding, respectively (in the case of hnRNP-U, e.g. the 198 amino acid N-terminal fragment, which was identified as the responsible fragment for binding to E3RS) is used as the major assay component. This complex, in the following termed "subject complex", is incubated with the test compound, while one of the interacting proteins carries a detectable marker and the other one is immobilized onto a solid support. Preferred markers are those producing a signal that can be easily measured in a high throughput screen. Examples for markers useful in the present invention are known in the art, they are selected from radioactive labels, e.g. $^{125}$Iodine, commercially available fluorescent markers for labeling proteins or peptides, e.g. Europium or the Green Fluorescent Protein (GFP), enzymes, e.g. luciferase, alkaline phosphatase etc.

The non-labeled protein partner is immobilized onto a solid support, either directly or through a tag. Suitable tags are commercially available, e.g. the FLAG, HA, MYC, HIS tag, etc.

Examples for solid supports useful in the invention are commercially available immunobeads or immunoplates, e.g. 96-well immunoplates, or microchips, which are coated with an antibody directed against one of the above-listed tags fused to the interacting protein.

The subject complex is preferably obtained by stoichiometric co-expression of hnRNP-U and E3RS, or a suitable fragment which is able to bind to the interaction partner, in a single host cell, e.g. a higher eukaryotic cell like a mammalian cell or an insect cell, or a yeast or a bacterial cell, according to routinely used expression methods (Current Protocols in Molecular Biology, Asubel et al., John Wiley and Sons, Inc.). The expression vehicle may be composed of a combination of commercially available standard expression plasmids carrying the cDNA of either partner protein (for hnRNP-U: Kiledjian and Dreyfuss, 1992, for E3RS: Yaron et al., 1998), e.g. as described in Example 2 and 3, or a bicistronic expression plasmid carrying both cDNA sequences (Gurtu, et al., 1996). To obtain the complex partners carrying a tag or a marker as described above, the cDNA may be cloned into an expression vector carrying the respective DNA sequence encoding the tag or marker, e.g. a commercially available FLAG, an enzyme (e.g. alkaline phosphatase), or GST vector, as described in the Examples.

The host cells are grown under standard conditions and the complex formed via co-expression of the two proteins is immunopurified according to known methods, e.g. affinity purification methods using FLAG immunobeads. The substrate complex may also be immobilized directly onto the immunoplates that are intended for use in the screening method, which obviates the need of a prior purification.

The two interacting proteins (or fragments thereof) may also be produced separately according to standard expression methods and then combined under conditions which allow the refolding that is necessary for stoichiometric interaction and thus formation of the subject complex, e.g. by using chaotropic agents such as guanidium isothiocyanate or guanidium hydrochloride.

Test compounds are allowed to interact with the subject complex for a period of time sufficient to allow for disruption of the complex, i.e. for approximately 2014 30 min. An agent that is known to induce dissociation of the complex serves as a positive control, e.g. a small molecule, pIκB (see Examples 4, 12) or a synthetic phosphopeptide containing the IκBα degradation motif, e.g. the phosphopeptide pp10 (Yaron et al., 1998), while non-phosphorylated IκBα or a non-phosphorylated IκBα peptide (e.g. p10 or p21, Yaron et al., 1997), or a modified IκBα peptide, e.g. a Ser-substituted peptide (p10S/E, Yaron et al., 1998) may be used as a negative control.

Upon incubation of the subject complex with a compound that exhibits the desired effect, i.e. an E3RS inhibitor, which interferes with the interaction of β-TrCP/E3RS and hnRNP-U, the complex partners dissociate. Aliquots of the dissociated protein that carries the detectable label are collected, preferably at predetermined time intervals, and the rate of signal emission (e.g. fluorescence or optical density changes, as a result of ongoing enzymatic reaction) is a measured, after transferring the labeled protein to a measurement plate or a membrane. The signal intensity and the rate of signal emission reflect the ability of a test compound to disrupt the hnRNP-U/E3RS complex.

This feasibility of this type of assay is exemplified by the experiment described in Examples 7 and 12, which demonstrates that the specific interaction that was shown to occur between a GFP-hnRNP-U or alkaline phosphatase-hnRNP-U fusion proteins and β-TrCP/E3RS can be abrogated by a specific 10 amino-acid pIκBα peptide (pp10), but not by a Ser-substituted peptide (p10S/E) (FIG. 7).

In an alternative embodiment, the subject complex used in the assay comprises three protein components, i.e. E3RS, hnRNP-U (or its N-terminal fragment) and Skp1. Since Skp1 facilitates the interaction of hnRNP-U with E3RS in vivo, incorporation of Skp1 into the subject complex more closely reflects the physiological situation. Therefore, obtaining a positive hit in such an assay is expected to more accurately predict the efficacy of the identified candidate inhibitor in therapy. This assay format has the potential to identify test compounds that either interferes directly with hnRNP-U/E3RS interaction, or indirectly by disrupting the Skp1/E3RS interaction. To obtain the three-component subject complex, the three proteins are produced by co-expression in a single cell, as described above for co-expression of hnRNP-U and E3RS. The cDNA of Skp1 is available from Bai et al. 1996. In Example 5, the preparation of a stoichiometric three-component complex is exemplified.

In a further embodiment, the disruption of the subject complex by an E3RS inhibitor is monitored by fluorescence measurements in solution. For this assay, none of the interacting proteins needs to be immobilized onto a solid support. One or both proteins are fused to a fluorescent label that emits a signal of different intensity or quality (e.g. a different emission wavelength) upon association or dissociation from the partner protein. A useful example for monitoring the interaction of the partner proteins is FRET, Fluorescence Resonance Energy Transfer. (Pollok, et al., 1999; Bastiaens, 1999; Feriasamy, et al., 1999). In this method, both partner proteins are labeled by a different fluorescent probe (e.g. Cyan Fluorescent Protein and Yellow Fluorescent proteins, commercially available from Clontech) and upon interaction, the fluorescence of one fluorophores is excited by intramolecular energy transfer.

Alternatively, the interaction of the proteins forming the subject complex, or the disruption of the complex is monitored by fluorescence polarization or fluorescence spin resonance, related techniques, based on quenching or quality changes of a fluorophore as a result of protein-protein association. Inclusion of an E3RS inhibitor into the assay will disrupt the subject complex, thereby affecting the emission of the fluorescence signal.

The above-described assays have the following advantages as compared to the assay described in WO 00/33447: (i) they require fewer components than the described E3-substrate interruption assay or the pIκBα ubiquitination assay (i.e., there is no need for any substrate, ubiquitination enzymes etc,) and therefore, the assays are simpler and more accurate; (ii) they obviate the need to prepare an IKK-phosphorylated substrate; (iii) they assay a low-affinity complex (relatively to the high affinity E3-pIκBα complex), which is more amenable for interruption, thus allowing the identification of a broader range of inhibitors.

In a further embodiment, the present invention provides a method for screening compounds that inactivate the protein hnRNP-U per se, i.e. its the chaperone and E3RS transporting activity. Such inactivation results in compromising either the association of E3RS with hnRNP-U or the dissociation of the two proteins upon interaction with the substrate pIκBα, such dissociation being necessary for pIκBα ubiquitination and degradation. In the following, this type of E3RS inhibitors, which target the chaperone and E3RS transporting activity of hnRNP-U, are termed "hnRNP-U inactivators". hn-RNP-U inactivators are expected to abolish or significantly diminish the inducible degradation of IκBα and thus NF-κB activation.

hnRNP-U inactivators can be identified in an assay, which is, in principle, set up in analogy to the above-described assays that employ the two-component or three-component subject complex to monitor E3RS/hnRNP-U dissociation. However, by contrast to the above assays, which identify compounds inducing dissociation of the subject complex, this assay variant is designed to identify compounds inhibiting dissociation of hnRNP-U from β-TrCP/E3RS. To detect hnRNP-U inactivators, the subject complex (comprising E3RS, hnRNP-U and optionally Skp1; or the fragments required for interaction, respectively) is incubated in the presence of the test compound, preferably after preincubation of hnRNP-U or a protein mixture containing it, e.g. a cell lysate, with the test compound, with an agent capable of inducing dissociation of the complex, evident by the release of the labeled component which generates a detectable signal, e.g. GFP fluorescence or radioactivity. Such an agent may be a pIκBα peptide, e.g. as described above, the pp10 peptide that contains the pIκBα degradation motif, or it may be selected from inhibitors identified in the above assays that monitor dissociation of the subject complex. The effect of the test compound on the dissociation of the complex is monitored; reduction of the signal generated by the release of the labeled protein is indicative of an hnRNP-U inactivating effect.

In an alternative embodiment, the invention relates to methods for identifying E3RS inhibitors that are based on cellular screening assay methods, which, as described above, exert their effect either by competing for or interfering with the interaction of hnRNP-U with E3RS or by inactivating hnRNP-U itself.

A cellular screening assay may be set up as follows: mammalian cells, e.g. 293 cells, expressing a labeled E3RS (e.g. GFP-E3RS, obtained upon transfection of the cells with a plasmid carrying a GFP-E3RS fusion construct) are grown in the presence of the test compound for a period of time sufficient for the compound to penetrate the cell and to exert its potential effect, which may be any period of time from approximately 30 minutes up to 16 hours. Then the cells are subject to immunoprecipitation according to standard methods with an antibody that binds to the complex, preferably an anti-hnRNP-U antibody, in order to pull down the hnRNP-U/E3RS complex. Anti-hnRNP-U (or anti-E3RS antibodies) can be obtained according to standard methods; they may be either polyclonal or monoclonal. Polyclonal antibodies are conventionally obtained by immunizing animals, particularly rabbits, by injecting the antigen or fragments thereof and subsequently purifying the immunoglobulin. Monoclonal antibodies may be obtained by standard procedures following the principle described by Köhler and Milstein, 1975. In Examples 4 and 9, monoclonal or polyclonal anti-hnRNP-U antibodies were shown to precipitate a complex composed of hnRNP-U, E3RS and other SCF components. If the test compound identified in the assay is an E3RS inhibitor, immunoprecipitation of hnRNP-U results in reduced coprecipitation of E3RS, leading to the absence or the reduction of a detectable E3RS signal. Alternatively, hnRNP-U may be used as the labeled complex partner and anti-E3RS antibodies are used to pull down the complex. Also in this case, the presence of an E3RS inhibitor will result in no detectable signal. A cellular screening assay that identifies hnRNP-U inactivators can be conducted according to this principle, with the modification that the assay is done in the presence of an agent inducing dissociation of the complex, as described above for the non-cellular assay.

In another embodiment a cellular assay for monitoring the interaction of hnRNP-U and E3RS is based on the above-mentioned FRET technique. Here, both partners are labeled by fluorescent labels, preferably through fusion with two different fluorescent proteins (e.g. YFP [Yellow Fluorescent Protein] and CFP [Cyan Fluorescent Protein]). This is achieved by way of transfection of the relevant expression plasmids (e.g. CFP-hnRNP-U and YFP-E3RS) into an appropriate cell (e.g. 293 cells). Following the transfection, cells expressing both labeled proteins are treated with test compounds and real-time measurement of FRET is performed in the treated cells. An E3RS inhibitor is expected to affect the FRET signal by disrupting the interaction of the labeled partner proteins (see for example: Degterev et al., 2001).

In a further embodiment, the invention relates to a cellular assay, which identifies E3RS inhibitors by identifying them as being compounds that have the ability of inhibiting Vpu-dependent CD4 degradation.

In this assay for identifying E3RS inhibitors, the mechanism of Vpu-mediated CD4 degradation is used as a surrogate for pIκBα degradation. In the following, is assay is termed "Vpu-mediated CD4 degradation assay", or simply "Vpu assay".

The Vpu-mediated CD4 degradation assay is based on the following considerations: Vpu is a small polypeptide encoded by HIV that resides in the membrane of the endoplasmic reticulum in infected cells and shares with IκB the DSGXXS degradation motif (Karin and Ben-Neriah, 2000). It simultaneously interacts with the CD4 protein and with β-TrCP/E3RS to form a ternary complex, which targets CD4 for proteasomal degradation (Margottin et al., 1998). Similarly to the interaction of pIκBα and hnRNP-U, β-TrCP/E3RS binds with Vpu via the WD40 domain of (Margottin et al., 1998) and requires phosphorylation at the two Ser residues of the shared motif. Whereas pIκBα is recognized and targeted by the E3RS for ubiquitination, Vpu is directing the E3 or the proteasome to an associated host protein, CD4. The overexpression of Vpu results in competitive inhibition of the hnRNP-U/E3RS interaction, which provides the basis for the Vpu assay to serve as a surrogate assay for identifying E3RS inhibitors.

In a preferred embodiment, the assay employs a mammalian cell line, e.g. 293 cells, that reports CD4 degradation upon Vpu induction (FIG. 7).

The reporter system comprises, as an essential feature, CD4 linked to a detectable label, e.g. in the form of a GFP-CD4 chimeric protein that fluoresces in the cell as long as it is stably expressed.

The construction of a plasmid encoding a Vpu-mediated degradable CD4 is based on the following considerations: The HIV Vpu is an endoplasmic reticulum (ER)-associated protein, which normally binds to the portion of the cellular CD4 that is retained in ER through a complex with the HIV gp160 protein. To circumvent the necessity for working with HIV infected cells, a CD4 plasmid is constructed to express CD4 modified by being fused to a marker protein, e.g. GFP (to this end, the cDNA sequence of CD4, which has been described by Maddon et al., 1985, is fused to the GFP sequence). This modified CD4 resides in the ER in the absence of gp 160. The human CD4 is truncated at its carboxy-terminal region, down to the amino-acid sequence KKTC, an ER retention signal. The N-terminal CD4 sequence, including the first three Ig-like domains (but preserving the CD4 signal sequence), is replaced with the marker sequence, e.g. the human GFP sequence, for allowing the quantitative measurement of the fusion protein through the signal, e.g. GFP fluorescence signal.

The test cell further contains a plasmid encoding the HIV Vpu polypeptide, the cDNA sequence of which is available (Terwilliger et al., 1989). Vpu is expressed under the control of a regulated, e.g. tetracycline-regulated, promoter. Vpu is expressed in the engineered cell line only when the expression modifier, e.g. tetracycline or doxycycline (DOX), which has, with respect to the so-called "tet-off" expression system, the function of a suppressor, is omitted from the medium. One of the advantages of this regulatable expression system is to avoid the toxicity caused byoverexpression of Vpu.

An alternative embodiment is based on the "tet-on" system, in which Vpu is only expressed in the presence of doxycycline. The principle of the assay is similar to that of the "tet-on" system, with the exception that doxycycline is inducing Vpu expression rather than suppressing it. Thus while in the "tet-off" system the removal of doxycycline is inducing Vpu, in the "tet-on" addition of doxycycline has a similar effect.

FIG. 7A illustrates the principle and function of this construct ("tet-off" system):

In the presence of the expression modifier (e.g. DOX) Vpu is not produced, therefore the modified CD4 is not degraded and produces a detectable signal, e.g. GFP fluorescence (A). Upon DOX withdrawal, Vpu is expressed, the modified CD4 protein is subject to E3RS-mediated degradation and the cell no longer emits a detectable signal, e.g. fluorescence (B). Incubation of the cells with a proteasome inhibitor, e.g. one of the inhibitors described in WO 95/25333 or by Lee and Goldberg (1998) serves as a positive control for the inhibition of CD4 degradation (C). Incubation with a compound, which has an E3RS inhibitory activity, results in the stabilization of the modified CD4 producing a detectable signal, e.g. fluorescence (D). The additional advantage of inducible Vpu expression is that in the absence of the expression modifier (DOX) the modified CD4 is maximally stabilized, producing the maximally emitted signal. This signal serves as a reference for the maximal effect of an E3RS inhibitory compound. Thus, this reporter system provides an additional advantage in that test compounds can be graded with respect to their inhibitory effect, which is directly proportional to the emitted fluorescence, this fluorescence can be readily detected and monitored by standard fluorescence readers, e.g. plate or filter readers (e.g. the Wallac Victor II instrument, which is suitable for high throughput screening). To exclude that the observed effect of the identified E3RS inhibitors, i.e. degradation of modified CD4, is non-specific, the inhibitors can be additionally tested while Vpu expression is suppressed, e.g. in the presence of DOX. Under these conditions, a specific E3RS inhibitor should not affect the intensity of the emitted signal. To exclude toxic effects on the test cells, a viability control may be additionally incorporated into the system, e.g. by expressing a red fluorescent protein (RFP). For that purpose, an RFP expression vector (commercially available, e.g. from Clontech) can be stably expressed in the assay cell line. Red fluorescence of the assay cell line should not be affected by a specific E3RS inhibitor. Therefore, the actual E3RS inhibitory effect of a compound can then be indicated by the GFP/RFP ratio, which must be smaller than one. Further validation of the E3RS inhibitory effect can be achieved in standard in vitro ubiquitination assays, as described e.g. by Yaron et al., 1998 (see also Example 4).

Compounds identified in the Vpu-mediated CD4 degradation assay can be confirmed to have an effect on the on the hnRNP-U/E3RS complex (either by affecting the association of the interacting partners, the stability of the complex or by inducing dissociation of the complex) using the above-described non-cellular or cellular assays that detect this effect.

On the other hand, E3RS inhibitors identified in the above-described assays according to their ability to affect hnRNP-U/E3RS interaction, either directly or indirectly, as described above, or the hnRNP-U inactivators described below, have the potential to be drug candidates also for the treatment of HIV-mediated diseases. The HIV inhibitory effect of these compounds can be further supported by subjecting them to the Vpu-mediated CD4 degradation assay, which is highly relevant to the mechanism of HIV pathogenesis (Lama et al., 1999).

In general, the cellular assays of the invention can be used as primary screening assays to detect active compounds, or as a means of confirming the activity of an E3RS inhibitor identified in a non-cellular assay (in this case they have the function of a secondary assay). Such assays can also be used to test the effect of an hnRNP-U antisense molecule, or an hnRNP-U inactivator developed on the basis of a rational design according to the crystal structure of the hnRNP-U/E3RS complex.

The cellular assays of the invention are unique in the sense that they report a distinct biochemical process within a cell: E3RS/hnRNP-U activity. The previously reported cellular assays (WO 98/36070 and WO 00/34447) are based on IκBα degradation, which requires signal-induced IKK activation for IκBα phosphorylation. The assays of the invention do not require IKK activation through cell stimulation. Furthermore, they provide the only kind of assay for identifying inhibitors of IκBα ubiquitination that can be adapted for high throughput screening, which can be achieved by monitoring an externally-emitted signal, e.g. a fluorescence signal, that is readily detectable by standard detection devices, e.g. plate readers or a fluorescent microscope. Evidently, the assay of the invention is distinct from any of the previously described assays for finding inhibitors of NF-B activation, e.g. those based on a κB reporter, which reflect any process that affects NF-κB activation (e.g. kinase activation, transcription modulation etc.) Another advantage of the assays of the invention lies in their potential to be applied for identifying inhibitors of cellular targets of HIV. These inhibitors are expected to be superior over other NF-κB inhibitors (e.g. IKK inhibitors) by inhibiting the function of both NF-κB and Vpu, which are necessary for HIV replication (Lama et al., 1999).

In a further embodiment, the invention relates to hnRNP-U inactivators, i.e. agents that exert their effect directly on the hnRNP-U protein or its expression.

Although the protein structure of hnRNP-U is unknown as yet, the sequence of the protein reveals features that allow for an assessment of the protein's structure-function relationship. Apart from the highly acidic N-terminal domain that has been shown to be responsible for interaction with E3RS, hnRNP-U contains a putative nucleotide-binding site (aa 485–492 (Kiledjian and Dreyfuss, 1992)). This motif is often associated with chaperone activity, including that of hsp90, which serves, similarly to hnRNP-U, as the "dedicated chaperone" for several signaling molecules (Buchner, 1999). Its interaction with certain oncoproteins, such as src and erb2 is essential for their transforming activity and in common with hnRNP-U it promotes the activity of these kinases only following its dissociation.

Two natural compounds, the macrocyclic antibiotic Radicicol and the benzoquinone ansamycin Geldanamycin tether the hsp90 at its nucleotide-binding site. As noted above, hsp90 and hnRNP-U have common functional features. It may be assumed that the hnRNP-U nucleotide-binding site has a role that is similar to the one in hsp90. Therefore, compounds structurally related to Radicicol and Geldanamycin are expected to be potential hn-RNP-U inactivators. The E3RS inhibitory effect of these agents or chemically modified derivatives thereof can be confirmed in one of the above-described cellular or non-cellular assays.

Considering the presence of a nucleotide-binding site in hnRNP-U, it may be assumed that certain hn-RNP-U inactivators may function similarly to hsp90 inhibitors of the benzoquinone ansamycin group by modifying the nucleotide-binding site. To confirm the relevance of the nucleotide-binding site in hnRNP-U for its chaperone function, site-directed mutagenesis can be used to abolish the putative function of this site. If this property is confirmed, its relevance is further evaluated by testing a potential nucleotide hydrolyzing activity of hnRNP-U. This can be done by standard ATP hydrolysis assays (Rosser and Nichitta, 2000). If the relevance of the nucleotide-binding site for the chaperone function of hnRNP-U is confirmed, the ATP hydrolyzing property can serve as the basis for another screening approach. In such an assay, hnRNP-U is tested for its ATP hydrolyzing activity, either on its own or in combination with one or more of its interacting partners, e.g. E3RS, optionally in conjunction with Skp1. The latter assay can also be conducted as a cellular assay, while the effect of a compound is tested on cells expressing tagged hnRNP-U, preferably also expressing the interacting partners. Following incubation with the compound, hnRNP-U is pulled down with an antibody as described above or with standard affinity matrix methods and assayed for nucleotide hydrolyzing activity.

hn-RNP-U inactivators may also be obtained by rational drug design based on the crystal structure obtained upon co-crystallizing hnRNP-U (or its N-terminal 198 aa fragment) and E3RS, preferably together with Skp1.

To date, attempts to generate a functional E3 from bacteria or other cellular sources, which are devoid of hnRNP-U, e.g. insect cells, have generally been unsuccessful.

One of the essential findings of the present invention is that hnRNP-U is crucial for the proper folding of E3RS. An important implication of this finding is that hnRNP-U may be required for expressing E3RS for crystallography analysis. Therefore, this finding represents the basis for providing a source for functional E3RS.

In order to obtain sufficient quantities of properly folded E3RS, E3RS is co-expressed with hnRNP-U, preferably together with Skp1, in the same cell, as described above for obtaining the subject complex, and the complex is obtained by one of the above-described affinity purification methods. Proper folding of E3RS is an absolute requirement for the crystallography analysis and is expected to be facilitated by interaction either with hnRNP-U. Since proper folding of E3RS may also be facilitated by one of its substrates, in the obtained complex, hnRNP-U can be exchanged by one of the E3RS substrates, e.g. pIκBα (see e.g. Example 4) or Vpu, or with a phosphorylated fragment of the substrates (e.g. the pp10, see Example 3), thereby preserving the correct folding of E3RS. An E3RS complex, either containing hnRNP-U, or an E3RS substrate, or a fragment thereof, can be obtained by standard methods of crystallography. Specialized molecular modeling techniques, including computer programs, may further be employed for designing E3RS inhibitors. See e.g. Cohen et al., 1990, Navia and Murcko, 1992. For example, where the structure of a test compounds is known, a model of the test compound may be superimposed over the model of the E3RS structure. A number of methods are known for this step, any of which may be used (see e.g. Farmer, 1980; U.S. Pat. Nos. 5,331,573; 5,500,807; Verlinde, 1994; and Kuntz, 1992). The model building techniques and computer evaluation systems described herein are not a limitation on the present invention.

Thus, using these computer evaluation systems, a large number of compounds may be quickly and easily examined.

Another class of hnRNP-U inactivators is hnRNP-U antisense oligodeoxyribonucleotides. Based on the hnRNP-U cDNA sequence, hnRNP-U antisense oligonucleotides can be obtained and assessed with regard to their pharmacological properties according to methods known in the art. "Antisense Technology", Methods in Enzymology, 2000 provides ample teaching for the person skilled in the art for the design, preparation, chemical modification and evaluation of the efficacy of antisense molecules, as well as their formulation and therapeutical application.

An example of an hn-RNP-U antisense molecule is the oligodeoxyribonucleotides AGGCGAGGAACTCATGGTGAG, which is directed against the sequence flanking the start codon of hnRNP-U. Several nucleotides of this molecule are modified, e.g. by phosphothioate or methyl groups to protect the molecule against degradation in the cell. The efficacy of an hnRNP-U antisense molecule can be determined by pIκBα degradation assays (Yaron et al., 1997 and 1998) and/or by one of the above-described cellular assays for E3RS inhibitors.

Another class of hnRNP-U cDNA inactivators, which function by inhibiting the expression of the RNA and/or protein are double stranded hnRNP-U cDNA molecules (RNAi) that interfere with hnRNP-U cDNA expression by ds-RNA mediated gene interference as described by Fire et al. 1998 and reviewed by Fire, 1999; Bosher and Labouesse, 2000; Sharp, 1999.

Further examples of E3RS inhibitors are synthetic peptides or phosphopeptides derived from the protein sequence of hnRNP-U, in particular the N-terminal acidic and Gln-rich domain of hnRNP-U, and from E3RS (e.g. pp1O, Yaron et al, 1998), peptidomimetic compounds resembling the hnRNP-U and E3RS inhibitory peptides and small molecules identified in this or the above-mentioned screens.

Further examples for E3RS inhibitory peptides are EDENGDDQGFQEGE (SEQ ID NO:1), DELGDEEE-GAGDE (SEQ ID NO:2), LDGDQMELGEEN (SEQ ID NO:3) and GISALDGDQMELGEENGAAGAA (SEQ ID NO:4) derived from the N-terminal region of hnRNP-U (Swissprot Q00839, see table 1). The peptides may be modified with penetratin, TAT, or a similar cell permeant vehicle, according to known methods, e.g. in analogy to the inhibitory peptides described by Dunican and Doherty, 2001.

Based on the amino acid sequence of hnRNP-U, in particular its N-terminal domain, peptidomimetics, e.g. with the amino acid sequence of the above-defined peptides, can be designed according to methods known in the art, as described e.g. by Kieber-Emmons et al., 1997.

In a further aspect, the present invention relates to a method for producing functional E3RS by co-expressing β-TrCP/E3RS with hnRNP-U, optionally together with Skp1, in bacterial, yeast or insect cells. Since hnRNP-U rescues the pIκBα-E3 activity from such cells devoid of hnRNP-U, this method enables the preparation of large quantities of a properly folded, functional E3RS for inhibitor screening, crystallography and other applications.

As noted above, the present invention is directed to screening methods for identifying compounds affecting the hnRNP-U/E3RS complex, which plays a major role in the signal-induced degradation of pIκBα and consequently NF-κB activation. Since the degradation motifs of IκBβ and IκBε are identical to the one of IκBα (Yaron et al., 1997) and E3RS was shown to be responsible also for the ubiquitination of IκBβ and IκBε (Hattori et al., 1999), the screening methods of the invention and the E3RS inhibitors which function by direct or indirect inactivation of hnRNP-U, may also be applied to inhibiting IκBβ and IκBε degradation.

The screening methods of the invention are generally useful for identifying modulators of ubiquitin-mediated proteolysis of phosphorylated IκB. Alternatively to screening for compounds that inhibit this process, the methods of the invention may be used for identifying compounds that upregulate it. The person skilled in the art can easily adapt the methods described above for this purpose by adapting the assay readout accordingly. Compounds that upregulate the E3RS pathway can be used for the treatment of disorders associated with E3RS dysfunction and thus NF-κB deficiency, or a disorder associated with inappropriate stabilization of an E3RS substrate, such as Familial Adenomatous Polyposis (FAP), which is a predisposition for colon cancer (Goss and Groden, 2000).

The transcription factor NF-κB is, inter alia, activated by treating cells with bacteriological stimuli (such as LPS), viruses (e.g. HIV virus type 1), viruses and viral products, parasites, inflammatory cytokines (e.g. TNF-α, TNF-β, IL-1, IL-2), T-cell mitogens (e.g. lectines), protein synthesis inhibitors (e.g. cycloheximide), physical stress (UV-light, gamma radiation), oxidative stress (e.g. hydrogen super oxide), chemotherapy, oncogenes and tumor promoters (e.g. Ras and phorbol ester) (Mayo, et al., 2000; Mercurio, et al, 1999; Lewis and Manning, 1999; Ghosh, et al., 1998).

NF-κB modulators, in particular inhibitors, have been suggested as drugs for the treatment of various pathological conditions in which the activation of NF-κB is involved.

Since E3RS inhibitors function as NF-κB inhibitors, the present invention relates, in a further aspect, to the use of E3RS inhibitors for the preparation of a medicament for the treatment of disorders associated with NF-κB activation. Examples of the numerous biomedically important conditions to which NF-κB contributes significantly as signal transducer and activator of immediate-early genes, and which may be treated by the application of an E3RS inhibitor, are the progression of AIDS, the activation of T-cells, B-cells and macrophages during the immune response, the so-called acute phase response, toxic shock, transplant rejection and the response of the cell to gamma radiation and UV light. E3RS inhibitors are, inter alia, expected to be effective as anti-inflammatory drugs, e.g. in the treatment of rheumatoid arthritis or asthma, in cancer therapy in order to increase the patient's sensitivity to chemotherapeutic agents, in the therapy of disorders of the central neural system, e.g. neurodegenerative diseases like Alzheimer, and stroke due to artherosclerosis, and as immune suppressive drugs.

It may be assumed that E3RS inhibitors cooperate with inhibitors of other components along the NF-κB activation pathway (e.g. IKK inhibitors) in blocking NF-κB activation. Recent clinical studies in cancer patients indicate that advanced tumors may easily evade the cytostatic effect of kinase inhibitors by acquiring inhibitor resistance mutations (Marx J., 2001). A combination of an E3RS inhibitor with a second NF-κB inhibitor that inhibits NF-κB activation by a mechanism that does not involve association of β-TrCP/E3RS with hnRNP-U, is expected to potentiate either compound's NF-κB inhibitory effect and/or to prevent the emergence of a cell resistant to the E3RS inhibitor and/or to the second NF-κB inhibitor. The likelihood of developing double resistance to both the E3RS and IKK inhibitor should be significantly lower than resistance to a single target blocker. Therefore, a combination of IKK and E3RS inhibitors is of particular value in therapy of proliferative diseases.

Although originally designed to modulate IκB degradation and NF-κB activation, E3RS inhibitors that have the capacity to disrupt the E3RS/hnRNP-U complex, can be further used to modulate other disease-associated processes. The disruption of E3RS/hnRNP-U will prevent the nuclear localization of E3RS (see Example 11), thus secluding E3RS from other potential nuclear substrates. An example of the latter is the stress response transcription factor ATF-4 (Lassot et al., 2001). As a result, these nuclear substrates will be spared from E3RS-dependent degradation, which may favorably affect a disease process; e.g. brain damage due to anoxia stress (Estes et al., 1995).

In a further aspect, the invention relates to a pharmaceutical composition, containing as its active ingredient an E3RS inhibitor, optionally in combination with a second NF-κB inhibitory compound that inhibits NF-κB activation by a different mechanism.

In order to be used as drugs for the treatment of NF-κB-related disorders, the E3RS inhibitors of the invention can be tested in animal models. The compound to be evaluated is applied to animal, e.g. by injection, which is subjected to an agent or another stimulus eliciting NF-κB activation in an organ or tissue of the animal, e.g. by applying LPS, which induces NF-K3 in the spleen. By comparing the degree of NF-κB activation with or without the inhibitor, the effect of the inhibitor can be determined. In parallel, the animal is monitored for symptoms that are typically associated with NF-κB activation, e.g. septic shock after LPS injection.

Toxicity and therapeutic efficacy of an E3RS inhibitor identified as a drug candidate can be determined by standard pharmaceutical procedures, which include conducting cell culture and animal experiments to determine the $IC_{50}$, $LD_50$, the $ED_{50}$. The data obtained are used for determining the human dose range, which will also depend on the dosage form (tablets, capsules, aerosol sprays, ampoules, etc.) and the administration route (oral, buccal, nasal, paterental or rectal). A pharmaceutical composition containing the compound as the active ingredient can be formulated in conventional manner using or more physiologically active carriers and excipients. Methods for making such formulations can be found in manuals, e.g. "Remington Pharmaceutical Sciences". Examples for ingredients that are useful for formulating the compounds identified according to the present invention are also found in WO 99/18193.

In order to verify in vivo that the compound exerts its effect via directly or indirectly compromising the E3RS/hnRNP-U complex, a tissue or blood sample is obtained from the animal or from the treated patient and subjected to hnRNP-U antibody precipitation, as described above. The E3RS activity within such precipitates is suitable as a parameter to monitor the efficacy of the drug; a compound exhibiting the desired effect is expected to abrogate the E3RS activity in the samples. The E3RS activity can be determined in a test according to principle described in Example 4. The significance of this type of assay lies in its ability to adjust the treatment using the inhibitors, e.g. the dosage and frequency of application. In addition, it can be used for optimizing the structure efficacy and/or formulation of the drug.

Based on the findings of the present invention, hnRNP-U antibodies can be used for diagnostic purposes, e.g. for identifying conditions in which the E3RS is compromised, e.g. by infectious agents or metabolic aberrations, which results NF-κB deficiency. A sample obtained from a patient suffering from such conditions will be examined with the aid of the hnRNP-U antibodies, as described above. The correction of an E3RS dysfunction, e.g. by reversing the metabolic aberration, can alleviate those symptoms that are secondary to NF-κB deficiency. E3RS analysis with the aid of anti-hnRNP-U antibodies is then used to indicate a successful correction of the metabolic disorder.

BRIEF DESCRIPTION OF THE FIGURES

FIG. 6: Failure to associate with hnRNP-U results in sequestration of E3RS in the cytoplasm. hnRNP-U, which is a nuclear scaffold-associated protein, could play a role in the subcellular localization of E3RS.

FIG. 8: Binding of E3RS to the acidic N-terminal domain of hnRNP-U

Figure 1:
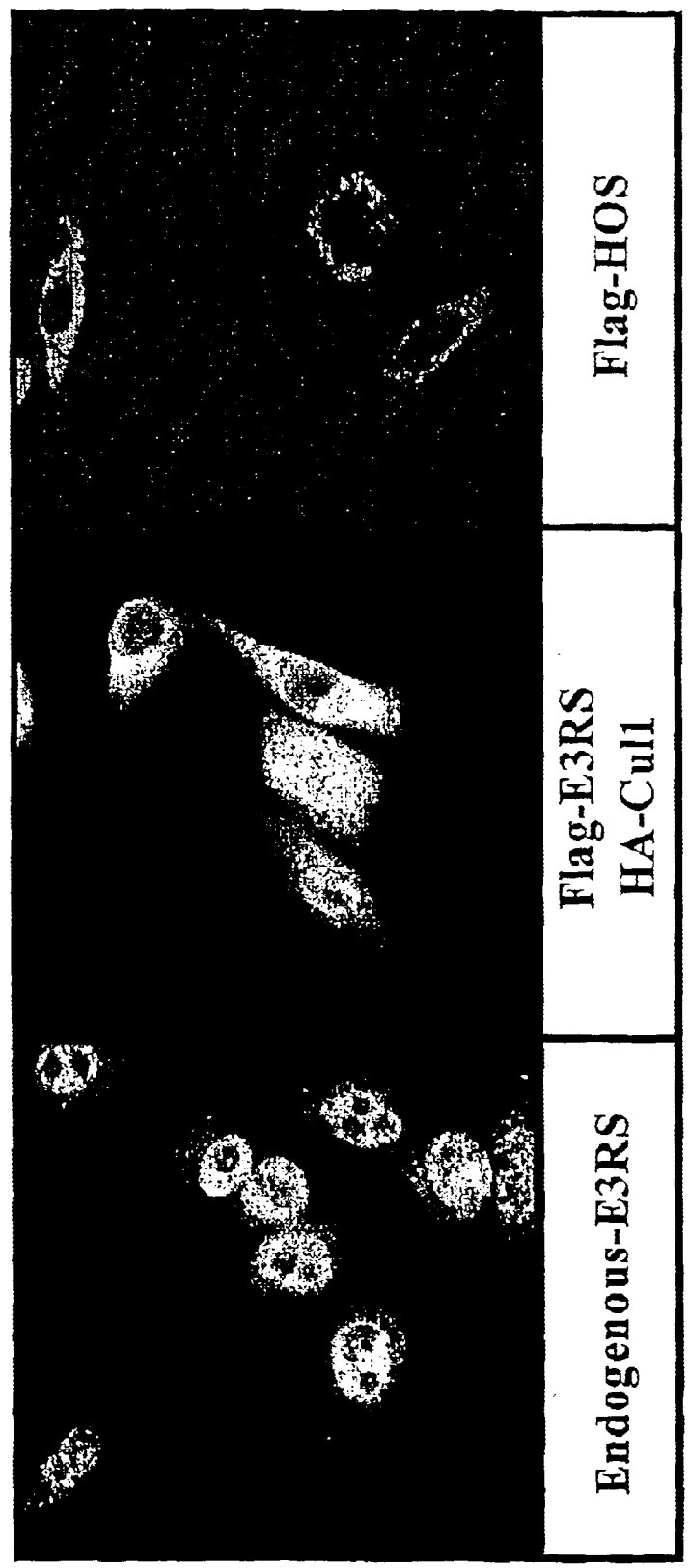
FIG. 1: E3RS resides predominantly in the nucleus

If not otherwise stated, the following Materials and Methods were used in the Examples:

a) Expression Vectors and Antibodies hnRNP-U was PCR-cloned from both human and mouse cDNA libraries into the pFLAG-CMV-2 expression vector (Kodak) at the Not1 site. The Not1 cleavage site was incorporated into both the forward primer, 5'tagcggccgcaatgagttcctcgcctgtt 3' (SEQ ID NO:6), and the reverse primer, 5' tagcggccgctcaataatatccttggtgata 3' (SEQ ID NO:7). The expression vectors encoding Flag-tagged E3RS/βTrCP (Flag-E3RS), the WD fragment (F-Box deleted E3RS) and the F-Box fragment (Flag-F-Box) are as described in (Yaron et al., 1998). HA-E3RS was prepared by subcloning human E3RS into the pCGN-HA vector. Mutagenesis of Lys 304 (K1) and Lys 326 (K2) residues to Ala in the Flag-WD construct was performed using the Quickchange kit (Stratagene). These were designated WDK1 and WDK2. The K2 residue in Flag-E3RS was similarly mutated to Ala (E3K2). Human HOS/β-TrCP2 cDNA was obtained by PCR-cloning according to Genbank entry AB033281 into the pFLAG-CMV-2 expression vector (Flag-HOS/β-TrCP2). HA-Cul1 and Myc-Skp1 expression plasmids were described by Lyapina et al., 1998). Flag-Smad 2 expression vector (Wu et al., 2000), used as a negative control. The MEKK1 and IKK2 mammalian expression plasmids are described before (Mercurio et al., 1997; Yin et al., 1998).

Anti-GFP affinity-purified monoclonal antibody was purchased from CLONTECH {Living Colors A.v. Monoclonal Antibody (JL-8) (1 mg/ml)}, and was used at a dilution 1:1000 (1 µg/ml) for Western Blot.

Agarose-conjugated (A-1205) and purified monoclonal anti-Flag M2 antibodies (F-3165) were purchased from Sigma. Monoclonal anti-hnRNP-U antibodies (3G6) were described by (Pinol-Roma et al., 1988). Sepharose-immobilized anti-p65 (anti-NF-κB) (sc-109 AC) and anti-HA (sc-805) were from Santa Cruz. Polyclonal anti-E3RS serum was obtained by immunizing rabbits with the E3RS N-terminal peptide (KALKFMNSSEREDCNNGEP; amino-acids 11–29 SEQ ID NO:5). Rabbit polyclonal anti-IκBα was described in (Alkalay et al., 1995). Rabbit anti-HA serum (sc-805) was purchased from Santa Cruz. Mouse monoclonal anti-Myc antibodies, c-myc(Ab-1), were from Oncogene Research Products. The goat anti-mouse RedX fluorescent secondary antibody is from Jackson (115-295-062) and goat anti-rabbit Alexa-488 from Molecular Probes (A-11008).

Polyclonal rabbit antiserum to human hnRNP-U was prepared against a fragment of hnRNP-U fused to GST. The GST fusion protein containing the carboxy-terminal half of the human hnRNP-U protein (amino-acids 406–806, contained in a BamH1-Bgl2 fragment of the human hnRNP-U) was prepared as follows: The fragment was inserted into the BamH1 site of a commercially available bacterial expression vector (pGEX1, Clontech). The fusion protein was purified from bacterial lysates using glutathione-agarose affinity chromatography and glutathione elution according to standard procedures. Rabbits were injected with the fusion protein in complete Freund's adjuvant and were bled following 3 boosts.

Anti-Vpu Rabbit polyclonal antibodies were prepared as follows:

An oligopeptide corresponding to amino acids 73–81 of the Vpu protein (encoded by the vpu gene of BH10 substrain of the IIIB HIV-1 isolate (Ratner et al., 1985) was conjugated to keyhole limpet haemocyanin and used to raise antibodies in three rabbits. After multiple injections of the antigen, the rabbits were shown to produce antibodies that recognize the oligopeptide. Serum from one of these rabbits that was shown to recognize in vitro translated vpu (Cohen, et al., 1988) was used (at a dilution of 1:1000) for Western Blot analysis.

b) Transfections and Immunofluorescence

CHO or 293T cells were plated out onto gelatin-coated plates and transfections performed using FuGENE 6 (Roche) or calcium phosphate. For heat shock treatment, at 24 h post transfection, the culture was supplemented with 50 mM Hepes in DMEM medium and heat shock performed for 1 h at 43° C. For immunofluorescence, cells were plated onto gelatin-coated cover slips and immunostaining was performed at 24 h post transfection. The cells were washed with phosphate buffered saline (PBS), fixed with 3% paraformaldehyde in PBS for 30 min at 4° C., permeabilized for 6 min using 0.25% Triton X-100 in PBS, and washed again with PBS. Blocking was done for 45 min with 10% goat serum in PBS-Tween 20 (0.1%). The primary antibodies anti-Flag (1:600), anti-HA (1:100) and anti-hnRNP-U (1:1000) were diluted in 5% bovine serum albumin, 1% Tween-20, PBS and incubated on the cover slips for 60 min. Cells were washed 3x with PBS, and then incubated with secondary fluorescent antibodies, goat anti-mouse RedX (1:150) or goat anti-rabbit Alexa-488 (1:100) for 45 min. Following 3 washes with PBS, the cover slips were mounted onto slides and analyzed by confocal microscopy.

c) Immunoprecipitation and Immunopurification

Cells were harvested 24–48 h after transfection, and extracted by suspension in 50 mM Tris pH 7.6, 1 mM dithiothreitol (DTT), 0.1% Nonidet P-40 (NP-40), 1 mM phenyl methyl sulfonyl fluoride, 1% Aprotinin and vortexing for 20 sec. Cell extracts were collected following centrifugation at 20,000 g for 30 min at 4° C. Cell extract (500 µg protein) was adjusted to 150 mM NaCl prior to immunoprecipitation. Flag-tagged proteins were immunoprecipitated with 2 µl of the anti-Flag immunobeads. Immunoprecipitation was for 2 h at 4° C. and the immunobeads were washed 4x in 300 mM NaCl, 1 mM DTT, 0.1% NP-40 and 50 mM Tris, pH 7.6. Flag-tagged proteins were eluted from the Flag immunobeads with 1 mg/ml of Flag peptide in 50 mM Tris, pH 7.6 for 30 min at 25° C. hnRNP-U was immunoprecipitated using 0.2–0.5 µl of the 3G6 antibody and 2–5 µl of Protein G immunobeads. Flag-E3RS or WD/hnRNP-U complex was disrupted by adding the phosphorylated IκB peptide pp10 (Yaron et al., 1998) to the extract at a concentration of 1 mg/ml during the immunoprecipitation. E3RS-associated proteins were eluted from the washed Flag immunobeads by incubating them with pp10 (1 mg/ml) for 30 min at RT. Control elutions were performed with the serine substituted IκBα peptide p10 S/E at similar conditions.

d) IκB Ubiquitination and Binding Assay

Flag-E3RS and endogenous hnRNP-U from 293T cells were used as an E3 source and Flag-WD was used as a negative control. 100 µg protein extract was immunoprecipitated using 2 µl anti-Flag beads or 0.21 µl anti-hnRNP-U antibodies. IκB was phosphorylated by the constitutively-active IκB kinase (IKK2; (Mercurio et al., 1997)) and subjected to binding and ubiquitination assays with each of the above E3 sources, as described previously by (Yaron et al., 1998).

e) Protein Identification

Mass spectrometric identification of proteins was done according to the strategy previously described (Shevchenko et al., 1996). Briefly, gel bands were excised from a one-dimensional gel stained with Coomassie coliloidal blue and digested in-gel with trypsin. The recovered unseparated peptide mixture was analyzed by MALDI mass spectrometry, using a Bruker Reflex III MALDI time-of-flight mass spectrometer (Bruker Daltronics, Bremen, Germany). Samples for MS/MS analysis were prepared essentially as described (Shevchenko et al., 1996). After in-gel digestion the supernatant was loaded onto a Poros R2 (Perseptive Biosystems, Framingham, Mass.) microcartridge (Wilm et al., 1996) and eluted into nanoelectrospray needles (Protana. Odense, Denmark). Nanoelectrospray MS/MS analysis was performed on a QSTAR quadrupole time-of-flight mass spectrometer (Perkin Elmer-Sciex, Ontario, Canada), and fragmentation spectra were obtained for as many peptides as possible. PepSea software (Protana) was used to search publicly available sequence databases maintained by NCBI with a list of peptide masses or with "peptide sequence tags" from fragmentation spectra.

f) Doxycycline-Inducible Vpu Expression System

The inducible system consists of the tetracycline (Tc)-responsive promoter system developed by Gossen and Bujard (1992). Vpu and GFP-CD4 expression were performed in either HeLa Tet-off gene expression system (CLONTECH). These stably transfected HeLa cells carry the pTet-Off regulator plasmid encoding a tetracycline-controlled transactivator (tTA), which also includes a neomycin-resistance gene. Alternatively 293 cells were transfected with the inducible constructs and the pTet-Off plasmid (Lavon et al., 2000).

The inducible p9CMVpu plasmid (A 292-bp DNA fragment encompassing nucleotide 5637 to 5929 (+1= transcription initiation site) and encoding the complete 81 amino acids Vpu protein of the HXBH10–vpu+ (Terwilliger et al. 1989) infectious molecular clone) was cloned downstream of a cytomegalovirus (CMV) minimal promoter fused to a tet operator sequences in pRep9 to generate p9CMVpu (Kobinger et al. 1997). The original neomycin resistance sequences in p9CMVpu with hygromycin resistance sequence.

Construction of an ER-Retained GFP-CD4 Fusion Protein:

In the first stage, a 100-bp leader sequence of the human CD4 gene (encoding the first 25 amino acids of the protein; Maddon et al. 1985) was PCR-cloned into BglII-BamHI linearized pEGFP-N1 vector (CLONTECH). Second, an AseI-BsrGI 1480-bp fragment (including the PCMV, CD4-leader and GFP coding sequences) from this vector was replaced with an AseI-BsrGI 1315-bp fragment (including the pCMV and GFP coding sequences) of a pEGFP-C1 vector (CLONTECH). This new fusion-vector was termed pCD4leader-EGFP-C1. Then, a 400-bp CD4 sequence (encoding amino-acids 311–425 of the protein; Maddon et al. 1985) was PCR-cloned into EcoRI-KpnI linearized pCD4leader-EGFP-C1 vector. This CD4 fragment includes the C2 Immunoglobulin-like extracellular domain (amino acids 311–376), the transmembrane domain (amino acids 377–398), and a cytoplasmic domain of CD4, in which the cytoplasmic C-terminal 13 amino acids were truncated. The last C-terminal amino acids, Lys-Lys-Thr-Cys, together with the transmembrane domain of this CD4 truncated molecule, are a signal for protein retention in the endoplasmic reticulum (Shin et al. 1991). This region of the CD4 protein was shown to be required, for Vpu-induced degradation of CD4 (Lenburg and Landau, 1993; Vincent et al. 1993).

EXAMPLE 1

E3RS Resides Predominantly in the Nucleus.

Current models imply that the major function of IκBα degradation is the exposure of the NF-κB nuclear localization signal (NLS), resulting in binding to importins and karyopherins and translocation of NF-κB from the cytoplasm into the nucleus (Karin and Ben-Neriah, 2000). Accordingly, one would suppose that the ubiquitin machinery operates in the cytoplasm, an assumption that could be confirmed by immunostaining of cells with antibodies directed against E3RS.

To investigate the localization E3RS, the following experiments were conducted: HeLa cells were immunostained for endogenous E3RS using rabbit anti-E3RS serum (FIG. 1A).

HeLa cells transfected with Flag-E3RS and HA-Cul1, were doubly stained with mouse monoclonal anti-Flag and rabbit polyclonal anti-HA as primary antibodies and goat anti-mouse Ig (Rhodamine) or goat anti-rabbit IgG (Alexa-488) as secondary antibodies (FIG. 1B). CHO cells transfected with Flag-HOS/β-TrCP2 were stained with anti-Flag antibodies (FIG. 1C).

Surprisingly, E3RS staining was mainly detected in the nucleus, whether observing the endogenous protein, or an epitope-tagged exogenously expressed one (FIGS. 1A,B). The amino-acid sequence of E3RS has no apparent nuclear localization motif (NLS). Therefore, its presence in the nucleus could be secondary to an associated protein, such as a component of the SCF complex. Yet, Cul1, an SCF component that carries the NLS, was mainly detected in the cytoplasm (FIG. 1B). Moreover, while all or most of the exogenously over-expressed E3RS was observed in the nucleus, only a minor fraction of it was found associated with other SCF components (data not shown), making it unlikely that E3RS is carried into the nucleus by the SCF complex. Of note is the finding that β-TrCP2/HOS, the closest homolog of E3RS, which, similarly to E3RS assembles into an SCF complex (Fuchs et al., 1999; Suzuki et al., 2000), was detected mainly in the cytoplasm (FIG. 1C).

EXAMPLE 2

Identification of hnRNP-U as the Major E3RS-Associated Protein.

To identify the E3RS transporting protein, a Flag-tagged E3RS was immunopurified from overexpressing 293 cells and analyzed by SDS-PAGE (FIG. 2A) and mass-spectrometry.

E3RS contains two protein-protein interaction modules, the F-box and the WD40 repeat domain (Margottin et al., 1998; Yaron et al., 1998). To determine which module was responsible for binding hnRNP-U, fragments composed of the F-box or the WD40 repeat (an F-box-deleted E3RS) were expressed separately, immunopurified and analyzed for hnRNP-U binding.

To this end, 293T cells were transfected with Flag-E3RS (lane 1), Flag-WD (lane 2), Flag-HOS/β-TrCP2 (lane 3), Flag-F-Box (lane 4), Flag-Smad-2 (lane 5) and HA-Skp2 (lane 6). The cells were lysed and the extracts immunoprecipitated, using agarose-conjugated anti-Flag (lanes 1–5) and anti-HA (lane 6) antibodies. Immunoprecipitated proteins were analyzed by SDS-PAGE and Coomassie Brilliant Blue staining. Molecular weight markers (kD) are indicated.

Figure 2A:
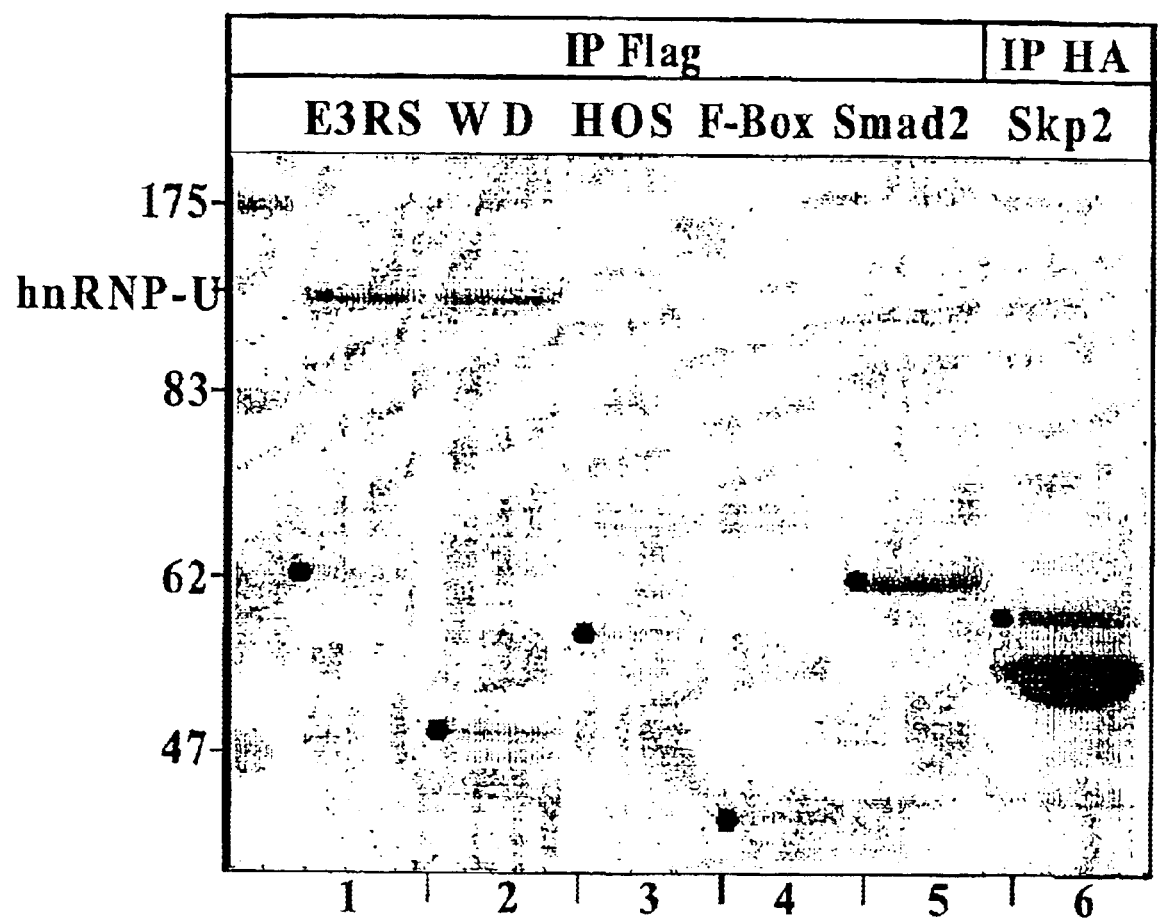
FIG. 2: Identification of hnRNP-U as the major E3RS-associated protein

It was found that a protein with the apparent molecular mass of 120 kD was specifically associated with E3RS at near stoichiometric ratio (Coomassie staining ratio of 1.5:1 for p120/E3RS; FIG. 2A, lane 1). Neither Skp2 (lane 6), another SCF-associated human F-box protein (Krek, 1998), nor β-TrCP2/HOS (lane 3), co-immunopurified with a similar 120 kD protein. Mass-spectrometry sequencing of the major E3RS-associated protein identified it as hnRNP-U (Kiledjian and Dreyfuss, 1992; Pinol-Roma et al., 1988), or scaffold attachment factor A (SAF-A) (Romig et al., 1992), an abundant nuclear protein.

The immunoprecipitated proteins were also analyzed by Western blot, using anti-Flag, anti-HA and monoclonal anti-hnRNP-U antibodies (FIG. 2B): The Western blot confirmed the specificity of hnRNP-U association: the protein signal was detected in association with E3RS, but not with β-TrCP2/HOS or Skp2.

In these experiments, hnRNP-U co-purified with the WD40-repeat (FIGS. 2A, lane 2, and 2B) but not with the F-box fragment (FIGS. 2A, lane 4, and 2B).

In a further experiment, Flag-tagged human and mouse hnRNP-U were co-transfected with HA-E3RS into 293T cells. Cell extracts were immunoprecipitated with anti-Flag antibodies and precipitated proteins analyzed by Western blot using anti-HA and anti-Flag antibodies.

It could be shown that human E3RS interacted with Flag-hnRNP-U of human and mouse origin (FIG. 2C), indicating a conserved interaction.

EXAMPLE 3
The E3RS-hnRNP-U Association Resembles an E3-Substrate Interaction It had been shown that the interaction of E3RS with its substrate is competitively inhibited by a short phosphorylated peptide representing the IκB degradation motif (Yaron et al., 1997; Winston et al., 1999). To determine whether the E3RS hnRNP-U association represents a receptor-ligand interaction, a complex composed of E3RS or its binding domain (F-box deleted E3RS, referred to as the WD-repeat fragment) and hnRNP-U, was incubated with the pIκBα peptide (FIG. 3A).

Flag-E3RS was immunoprecipitated with anti-Flag immunobeads in the absence (lane 1), or presence (lane 2) of a phosphorylated IκBα peptide (pp10, containing the IκBα degradation motif). Flag-WD was immunoprecipitated with anti-Flag immunobeads with no peptide (lane 3), in the presence of pp10 (lane 4), or in the presence of the serine/glutamic acid-substituted peptide p10 S/E (lane 5) and the immune-complexes were analyzed by SDS-PAGE and Coomassie-Blue staining.

Figure 3A:
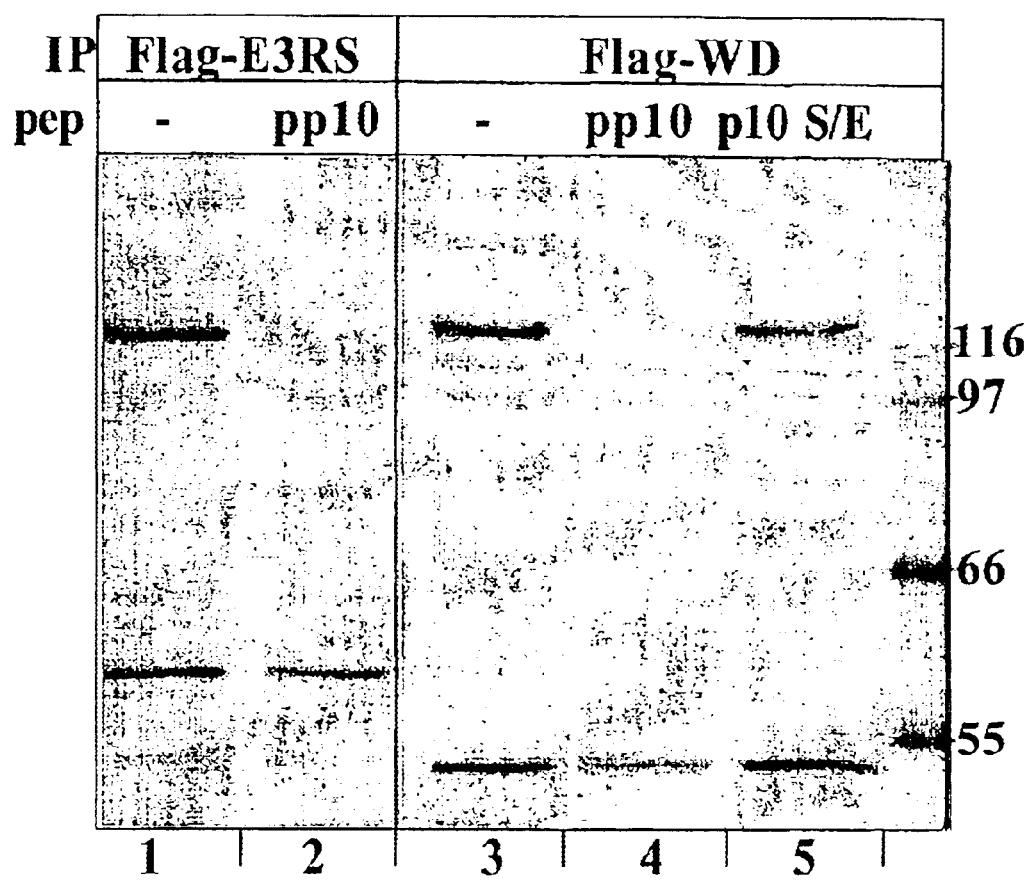
FIG. 3: The E3RS-hnRNP-U association resembles an E3-substrate interaction

This experiment showed that the pIκB peptide disrupted the interaction of hnRNP-U with E3RS (FIG. 3A, lane 2), or its WD fragment (FIG. 3A, lane 4), while an S/E substituted IκBα peptide had no effect on the complex (FIG. 3A, lane 5).

It had been suggested that the specific association between the WD40 repeat domain of E3RS and hnRNP-U may resemble the interaction of the β-transducin WD-repeat with γ-transducin (Sondek et al., 1996). Several residues within the α helix loops of the first WD repeat contribute to this specific interaction (Lambright et al., 1996; Sondek et al., 1996). To test this possibility, two E3RS lysine residues corresponding to similar residues of β-transducin that play a role in γ-transducin association were substituted through mutagenesis. Flag-WD (FIG. 3B, lanes 1–3), and the two Flag-WD mutants, WDK1 (FIG. 3B, lanes 4–6) and WDK2 (FIG. 3B, lanes 7–9) were immunopurified using anti-Flag immunobeads. To detect specifically dissociated proteins, immunobeads were incubated with Flag peptide (FIG. 3B, lanes 1,4,7), pp10 (FIG. 3B, lanes 2,5,8), p10S/E (FIG. 3B, lanes 3,6,9) and the post-slurry fractions were separated by SDS-PAGE. WD-associated polypeptides were visualized by Coomassie staining and the indicated bands (marked 1–18) were analyzed by mass-spectrometry. The results of the mass spectrometry analysis are depicted in Table 1. Molecular weight markers (kD) are indicated.

While substitution of one of these lysine residues (K1, Lys 304) by alanine had no apparent effect on binding hnRNP-U (FIG. 3B, lane 4), the substitution of Lys 326 (K2) abrogated hnRNP-U binding (FIG. 3B, lane 7). The overall pattern of the WD40-repeat-associated proteins varied remarkably between WT WD and WDK1 on the one hand (lanes 1,4) and WDK2 on the other (lane 7). The majority of the WT WD-associated proteins, apart from hnRNP-U, were other hnRNP proteins, while all of the mutant WD associated proteins were known chaperonins, mostly heat shock proteins and T-complex proteins (TRiC) (see Table 1). With the exception of Hsp70 and Hsc70, which dissociated from the WDK2 mutant protein in the presence of either wild type or mutant IκBα peptides (FIG. 3B, lanes 8,9), none of the other chaperonins detached from the mutant WDK2 fragment in the presence of any peptide. This is in contrast to the specific dissociation of hnRNP-U in the presence of the pIκBα peptide (FIG. 3B, lanes 2,5), indicating that the nature of the interaction between hnRNP-U and the WD domain of E3RS is distinct from the association of the latter with any of the chaperonins.

Considering the failure of the WDK2 mutant to bind hnRNP-U (FIG. 3B, lane 7), the effect of the Lys mutants on the binding of pIκBα was examined. Flag-tagged proteins WD, WDK1, WDK2 and E3RS were immobilized on anti-Flag immunobeads and then incubated with IKK-phosphorylated (pIκBα) or non-phosphorylated $^{35}$S-labeled IκBα. The beads were washed extensively and associated proteins analyzed by SDS-PAGE and phosphorimaging. The results of this experiment are shown in FIG. 3C: The WDK1 mutant was indistinguishable from WT E3RS or its WD fragment in binding pIκBα, while the WDK2 mutant failed to bind pIκBα. Hence, the capacity of the E3RS binding domain to interact with pIκBα paralleled hnRNP-U binding, suggesting an E3-substrate relationship for both pairs of molecules. Overall, FIG. 3 shows that the E3RS-hnRNP-U complex dissociates in the presence of pIκBα peptide and is abrogated by a specific WD-repeat mutation.

Nevertheless, whereas the interaction of E3RS with pIκBα resulted in the destruction of the latter (unless stabilized by proteasome inhibitors), hnRNP-U association with E3RS was stable, both in vivo (FIGS. 2,3) and in vitro. Prolonged incubation of the E3RS/hnRNP-U complex in ubiquitination buffer supplemented with E1 and several E2s (Ubc5C, UbcH7 and Ubc3), had no effect on hnRNP-U stability, nor were any hnRNP-U-ubiquitin species detected in the assay (data not shown). These observations suggest that hnRNP-U is not a true SCF$^{\beta-TrCP/E3Rs}$ substrate.

EXAMPLE 4 hnRNP-U Delivers an Active SCF$^{\beta-TrCP/E3Rs}$ complex to the ubiquitination substrate.

The specific association of hnRNP-U with E3RS suggested the possibility of engaging an active pIκBα ligase through the hnRNP-U protein.

Figure 4A:
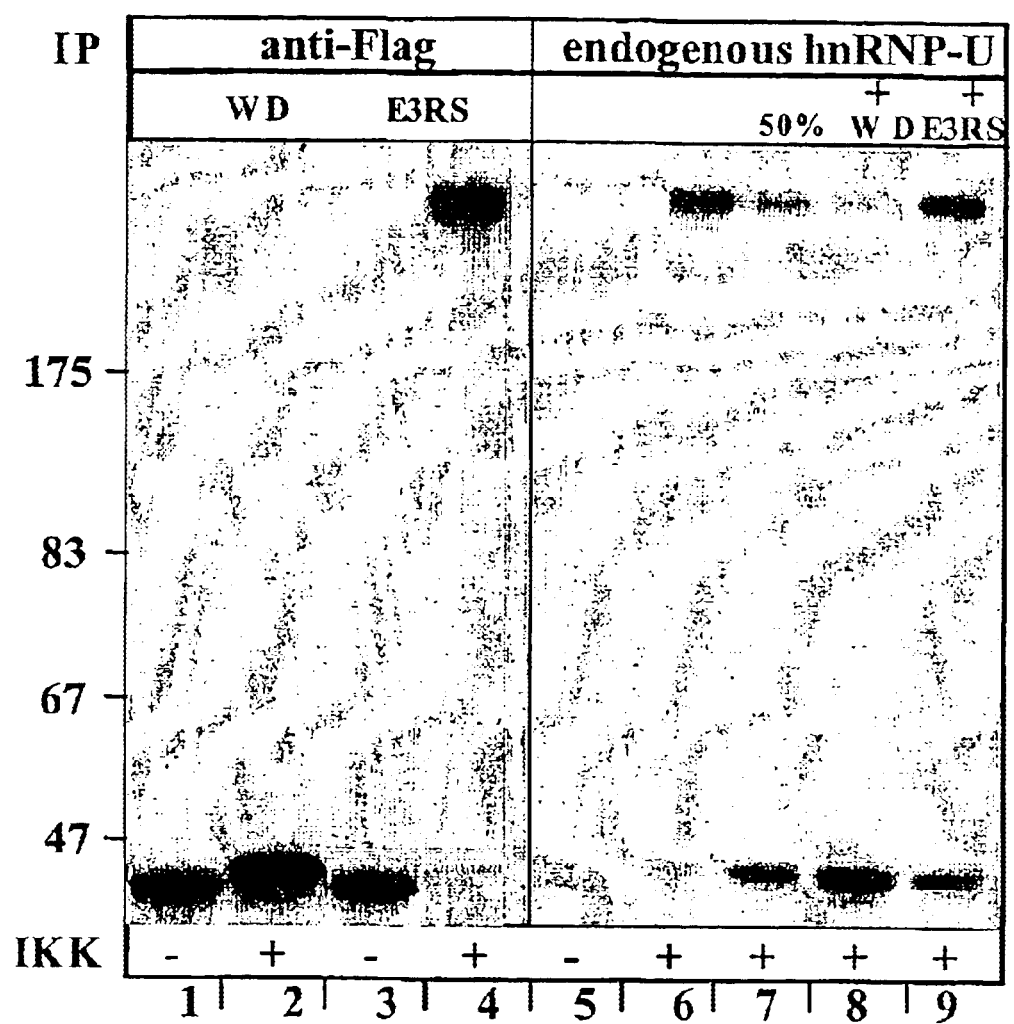
FIG. 4: hnRNP-U delivers an active SCF-TrCP/E3RS complex to the ubiquitination substrate

$^{35}$S-labeled pIκBα (IKK-phosphorylated; lanes 2,4,6–9) or IκBα (FIG. 4A, lanes 1,3,5) were assayed for ubiquitination, using as an E3 source, Flag-E3RS (FIG. 4A, lanes 3,4), Flag-WD (F-box-deleted E3RS as a negative control; FIG. 4A, lanes 1,2), immunoprecipitated endogenous hnRNP-U from non-transfected cells (FIG. 4A, lanes 5–7; lane 7 employed 50% of the E3 source of lane 6), or from cells transfected with WD (FIG. 4A, lane 8) or E3RS (FIG. 4A, lane 9). Molecular weight markers (kD) are indicated.

This experiment shows that immunoprecipitated hnRNP-U (the endogenous protein, FIG. 4A, lane 6) was as efficient as transfected E3RS (FIG. 4A, lane 4) in providing an E3 source for pIκBα ubiquitination. hnRNP-U-mediated pIκBα ubiquitination was E3RS-dependent, since co-expression of the E3RS-WD40 repeat fragment, completely suppressed it (FIG. 4A, lane 8). The ability of the pIκBα peptide to compete with hnRNP-U for binding to E3RS, suggested that the interaction of E3RS with the two proteins, pIκBα and hnRNP-U, is mutually exclusive.

Figure 4B:
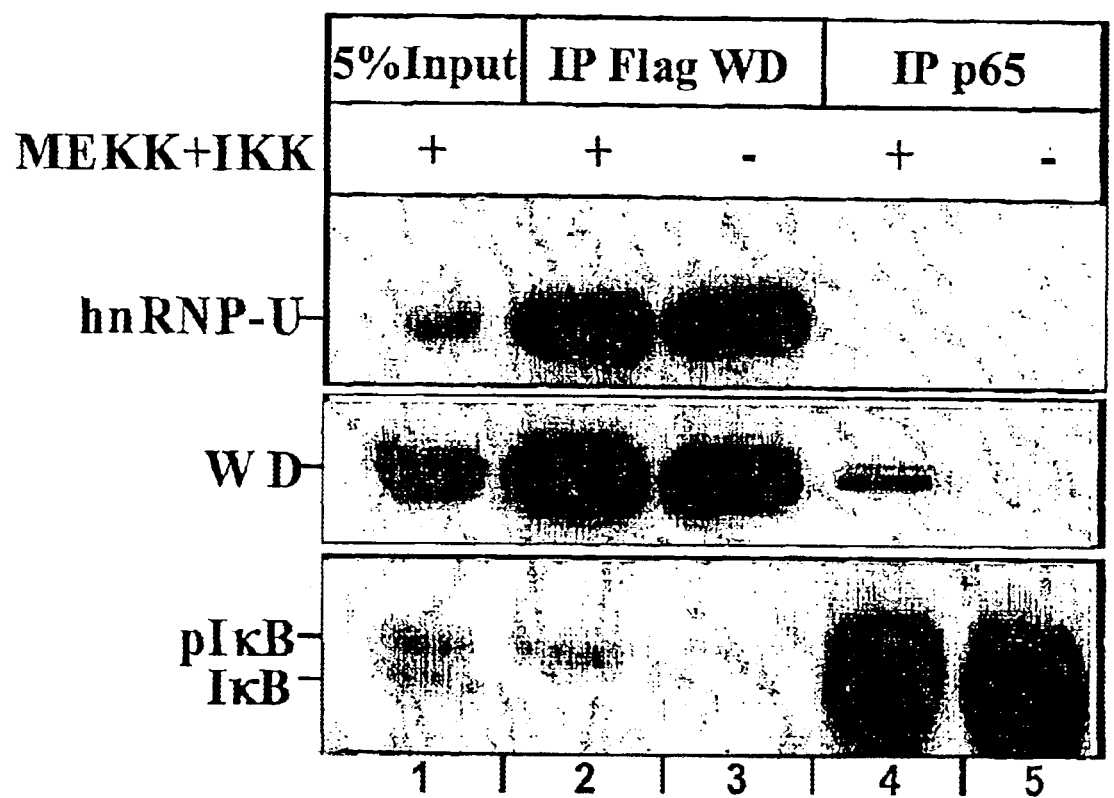

To confirm this observation, phosphorylated IκBα was induced in vivo by co-expressing MEKK1 and IKK2 in 293 cells (Hatakeyama et al., 1999; Lee et al., 1998), immunopurified through the NF-κB complex and its associated proteins analyzed by Western blot (FIG. 4B).

Specifically, 293T cells were transfected with Flag-WD and HA-hnRNP-U with or without constitutively active MEKK and IKK2 (a kinase combination that induces IκBα phosphorylation). Cell lysates (5% input is shown) were immunoprecipitated using anti-Flag (FIG. 4B, lanes 2,3) and anti-p65 (FIG. 4B, lanes 4,5) and the immune complexes were analyzed by Western blot with anti-Flag, anti-HA and anti-IκBα antibodies. A co-expressed WD fragment was found to associate with pIκBα (FIG. 4B, lane 4), but not with a non-phosphorylated IκBα (FIG. 4B, lane 5). Yet, in spite of the stoichiometric association with the WD fragment prior to interacting with pIκBα, no hnRNP-U was detected in the pIκBα complex (FIG. 4B, lane 4), indicating that E3RS was incapable of simultaneous engagement with hnRNP-U and pIκBα and, therefore, has no direct role in pIκBα ubiquitination.

Nevertheless, hnRNP-U could play a role in delivering either E3RS or the whole SCF complex to the substrate towards ubiquitination. Immunoprecipitation analysis of the endogenous hnRNP-U from SCF transfected cells revealed several SCF components (FIG. 4C):

293T cells were transfected with HA-Cul1 and Myc-Skp1 alone (lanes 1,4), or together with Flag-E3RS (lanes 2,5) or with Flag-E3RS alone (lanes 3,6). Cell lysates (5% input is shown) were immunoprecipitated with monoclonal anti-hnRNP-U antibodies and analyzed by Western blot with the relevant antibodies. Molecular weight markers (kD) are indicated.

While only minute amounts of Skp1 and Cul1 associated with hnRNP-U in the absence of exogenous E3RS, significantly higher levels of these components were pulled down through hnRNP-U upon E3RS overexpression (compare lanes 4 and 5 of FIG. 4C). It, therefore, appears that all the interactions of SCF components with hnRNP-U are via E3RS.

Next, 293T cells transfected with Flag-E3RS were immunoprecipitated using anti-Flag (lanes 1,2) or anti-hnRNP-U (FIG. 4D, lanes 3–7) antibodies. IκBα (FIG. 4D, lanes 1,3,4) and IKK phosphorylated IκBα (pIκBα; FIG. 4D, lanes 2,5–7) were incubated with the immunobeads, after which, both the immunobeads (slurry (S); FIG. 4D, lanes 1–3,5) and the post-slurry fractions (PS; FIG. 4D, lanes 4,6) were analyzed by Western blot directly, or after immunoprecipitation of the post-slurry fraction (same as in FIG. 4D, lane 6) with anti-Flag beads (FIG. 4D, lane 7).

The results of these experiments were as follows: E3RS-anchored complex bound pIκBα (FIG. 4D, lane 2), but not the non-phosphorylated IκBα (FIG. 4D, lane 1). Yet, anchoring the same complex through hnRNP-U, resulted in failure to bind any IκBα species (FIGS. 4D, 4D, lanes 3,5). Instead, pIκBα (FIG. 4D, lane 6), but not IκBα (FIG. 4D, lane 4) induced the dissociation of the E3RS from the immobilized hnRNP-U into the post-slurry fraction. The co-immunoprecipitation of E3RS with pIκBα from the post-slurry fraction (FIG. 4D, lane 7 shows that the dissociation of E3RS from hnRNP-U was coupled to the binding of pIκBα. Taken together, these results suggest that the role of hnRNP-U in pIκBα ubiquitination is to deliver an active E3 to the substrate, following which it dissociates from the ligase.

EXAMPLE 5

Skp1 facilitates hnRNP-U association with E3RS and reverses the binding defect imposed by a specific E3RS mutation.

Figure 5:
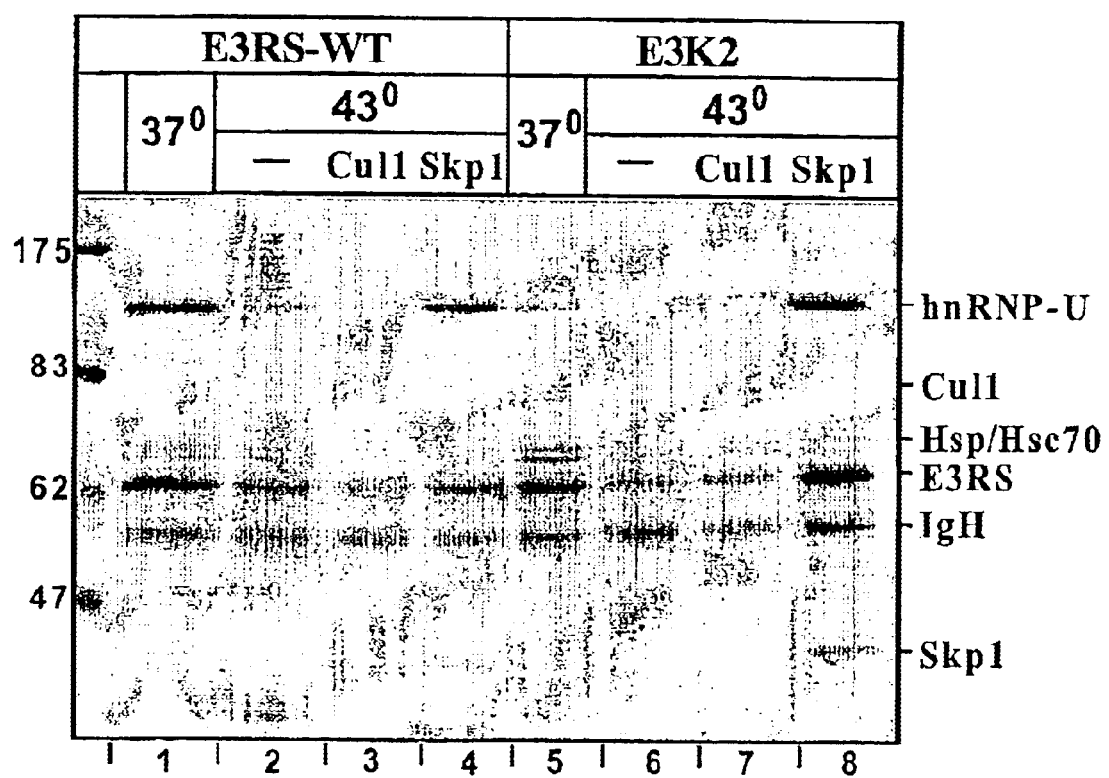
FIG. 5: Skp1 facilitates hnRNP-U interaction with E3RS and reverses the binding defect imposed by a specific E3RS mutation

A K2 mutant was constructed in the context of full-length E3RS (designated E3K2) and tested for hnRNP-U and pIκBα binding. 293T cells were transfected with Flag-E3RS alone (lanes 1,2) or together with Myc-Cul1 (FIG. 5, lane 3) or Myc-Skp1 (FIG. 5, lane 4); with Flag-E3K2 alone (FIG. 5, lanes 5,6) or together with Myc-Cul1 (FIG. 5, lane 7), or Myc-Skp1 (FIG. 5, lane 8). In an attempt to expose the effect of the mutation, cells harboring the mutant or WT E3RS were subjected to heat shock (43° C. for 60 min1 h prior to cell lysis; lanes 2–4, 6–8). Protein complexes were immunoprecipitated using anti-Flag and analyzed by SDS-PAGE and Coomassie-Blue staining. Molecular weight markers (kD) are indicated.

Surprisingly, the K2 mutant retained the capacity to bind pIκBα (data not shown) and hnRNP-U (FIG. 5, lane 5), although at 20% efficiency, compared with WT E3RS (lane 1). The heat shock resulted in the inability of the mutant protein to bind hnRNP-U (lane 6), while the WT E3RS retained 30% hnRNP-U binding (lane 2). There was no effect on the pIκBα binding capacity of WT E3RS, whereas the mutant protein lost 50–60% of its binding capacity (data not shown). Since an identical mutation in the F-box-deleted E3RS exhibited a complete loss of binding to both pIκBα and hnRNP-U, the question was whether the F-box plays a role in compensating for the loss of function mutation. Studies of Cdc4-Sic1 interactions in yeast indicated that the binding of Skp1 to the F-box module facilitated substrate binding (Feldman et al., 1997; Skowyra et al., 1997). Hence, a complex relationship might exist between the F-box and the WD40 repeat module, which could affect the performance of E3K2. Obviously, the levels of endogenous SCF components were not sufficient to saturate the overexpressed E3RS mutant (not shown).

Therefore, to evaluate the role of the SCF assembly in substrate binding, either Skp1 or Cul1 together with E3RS were co-expressed and the latter was tested for hnRNP-U and pIκBα binding following heat shock treatment. Skp1, but not Cul1, enhanced the association of hnRNP-U with WT E3RS at 43° C. (FIG. 5, lanes 3,4) and restored full hnRNP-U association (lanes 7,8) and pIκBα binding (data not shown) of the mutant protein. The effect of Skp1 was maximal upon stoichiometric association with E3RS (lane 4), suggesting that the interaction of hnRNP-U with E3RS requires a ternary complex, including Skp1.

EXAMPLE 6

Failure to associate with hnRNP-U results in sequestration of E3RS in the cytoplasm.

It was hypothesized that hnRNP-U, which is a nuclear scaffold-associated protein (Romig et al., 1992), could play a role in the subcellular localization of E3RS.

To test this, HeLa cells (FIGS. 6A,B) were doubly immunostained for the endogenous hnRNP-U together with endogenous E3RS (FIGS. 6, A) or transfected HA-E3RS (FIG. 6B). CHO cells (FIGS. 6C–L) were immunostained for the following Flag-tagged proteins: F-Box (FIG. 6C), WD (FIG. 6D), WDK1 (FIG. 6E) and WDK2 (FIG. 6F). Cells transfected with Flag-E3RS (FIGS. 6G,J) or Flag-E3K2 (FIGS. 6H,K) were incubated at 37° C. (FIGS. 6G,H) or at 43° C. (FIGS. 6J,K) for 1 h before staining. Cells transfected with Flag-E3K2, together with HA-Cul1 (FIG. 6I), or Myc-Skp1 FIG. 6L), were incubated at 43° C. for 1 h before immunostaining.

Close observation of the relationship of the endogenous E3RS and hnRNP-U under a confocal microscope indicated colocalization in discrete speckles, many of them in close proximity to the nuclear membrane (FIG. 6A). A similar molecular relationship was observed when analyzing transfected E3RS together with the endogenous hnRNP-U (FIG. 6B). To understand the basis of colocalization, the subcellular residence of WT and mutant E3RS or of fragments harboring distinct domains of these proteins, was determined in connection to their capacity to interact with hnRNP-U. Whereas the E3RS F-box fragment was exclusively cytoplasmic (FIG. 6C), the hnRNP-U associated WD fragment and WDK1 were observed in the nucleus (FIGS. 6D,E). However, whereas WDK2 was exclusively cytoplasmic (FIG. 6F), E3K2 was mostly (~75%) nuclear (FIG. 6H). Bearing in mind the fragile interaction of E3K2 with hnRNP-U, we examined its subcellular localization following heat shock treatment and interaction with Skp1 or Cul1, procedures that affect the interaction of the mutant E3RS with hnRNP-U (FIG. 5). While the nuclear localization of the WT protein was minimally reduced by heat shock (FIG. 6J), the localization of E3K2 shifted from predominantly nuclear (6H) to mostly cytoplasmic at 43° C. (FIG. 6K). Co-expression of Skp1 (FIG. 6L), but not of Cul1 (FIG. 6I), drove it back to the nucleus. Therefore, there appears to be a tight correlation between hnRNP-U binding and nuclear localization of the E3RS molecules: molecules or fragments that associate with hnRNP-U, either on their own (WT WD fragment and WT or E3K2 at normal temperature), or with the assistance of Skp1 (E3K2 mutant following heat shock treatment), reside in the nucleus.

EXAMPLE 7

In Vitro E3 Inhibition Assay

E3RS inhibitors induce the dissociation of GFP-hnRNP-U. A complex of Flag-β-TrCP/E3RS and GFP-hnRNP-U or Flag-βp-TrCP/E3RS with the endogenous hnRNP-U was immunoprecipitated from 293 transfectants with anti-Flag antibodies, eluted with a Flag peptide, with pp10 (an E3RS-blocking peptide), or with the p10S/E control peptide and the eluted fractions were separated by SDS-PAGE. Using monoclonal anti-GFP antibodies (Clontech), GFP-hnRNP-U was detected by Western blotting using pp10, but not p10S/E, indicating the specific dissociation of GFP-hnRNP-U from E3RS, similarly to the dissociation of the endogenous hnRNP-U. GFP-hnRNP-U dissociation can, therefore, fatefully report the capacity of a peptide or similar E3RS-interacting molecule to competitively block the E3RS binding sites. As similar peptides were previously used to block NF-κB activation in stimulated cells (Yaron et al., 1997), the GFP-hnRNP-U dissociation assay or a similar assay, based on the fluorescence signal of the GFP, can indicate the capacity of NF-κB inhibition by specific compounds.

EXAMPLE 8

Figure 7A:
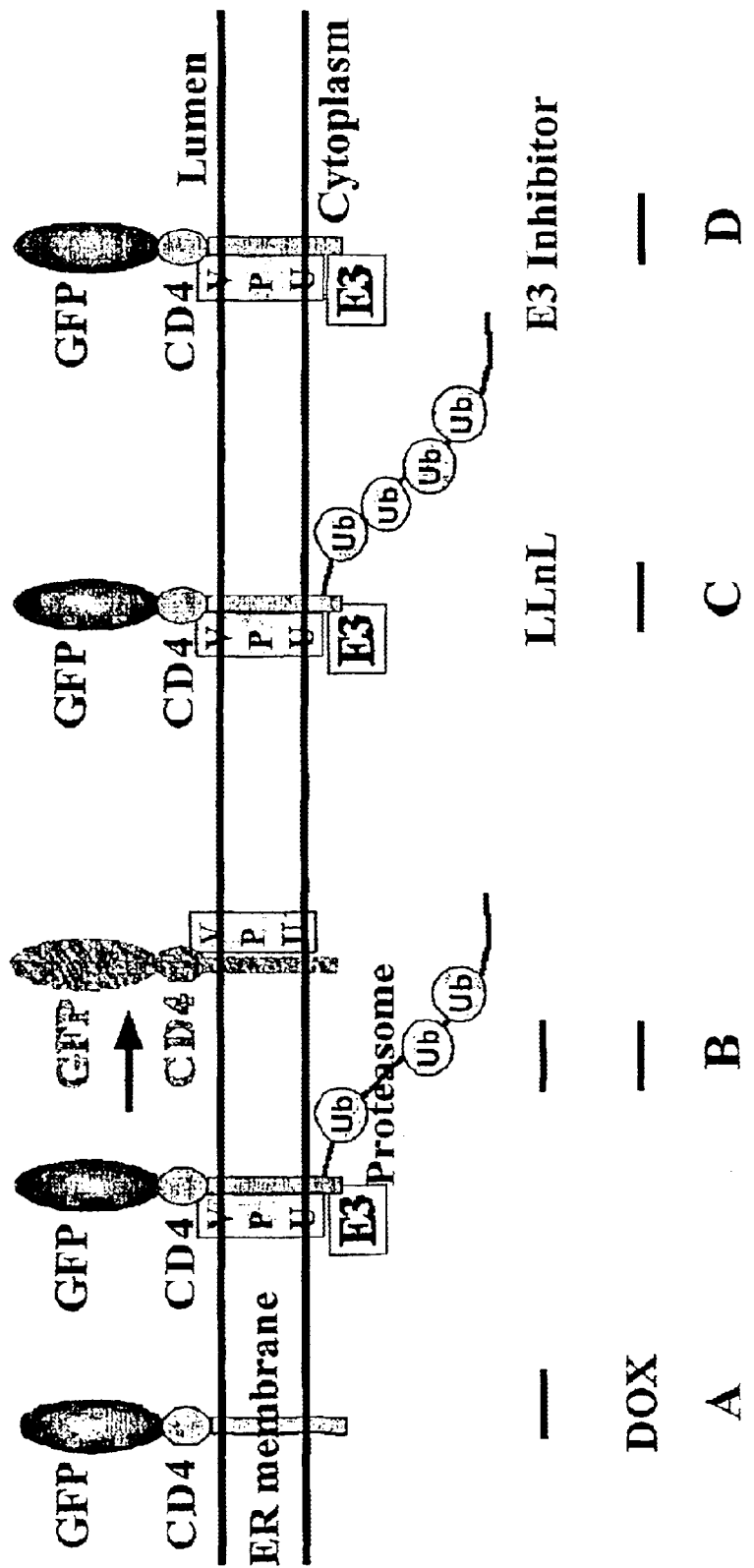
FIG. 7: Vpu-mediated CD4 degradation assay

A cellular assay for monitoring the E3RS-hnRNP-U ubiquitin-ligase activity, based on HIV Vpu-mediated CD4 degradation The ubiquitin-ligase activity is measured as a function of Vpu-mediated GFP-CD4 degradation (FIG. 7A). The HIV Vpu is an endoplasmic reticulum (ER)-associated protein, which normally associates with the portion of the cellular CD4 that is retained in ER through a complex with the HIV gp 160 protein. To circumvent the necessity for working with HIV infected cells, The GFP-CD4 plasmid was constructed to express the GFP fusion protein in the ER in the absence of gp160. The human CD4 was truncated at its carboxy-terminal region, down to the amino-acid sequence KKTC, an ER retention signal. The N-terminal CD4 sequence, including the first three Ig-like domains (but preserving the CD4 signal sequence), was replaced with the human EGFP sequence for allowing the quantitative measurement of the fusion protein through the GFP fluorescence signal.

Figure 7B:
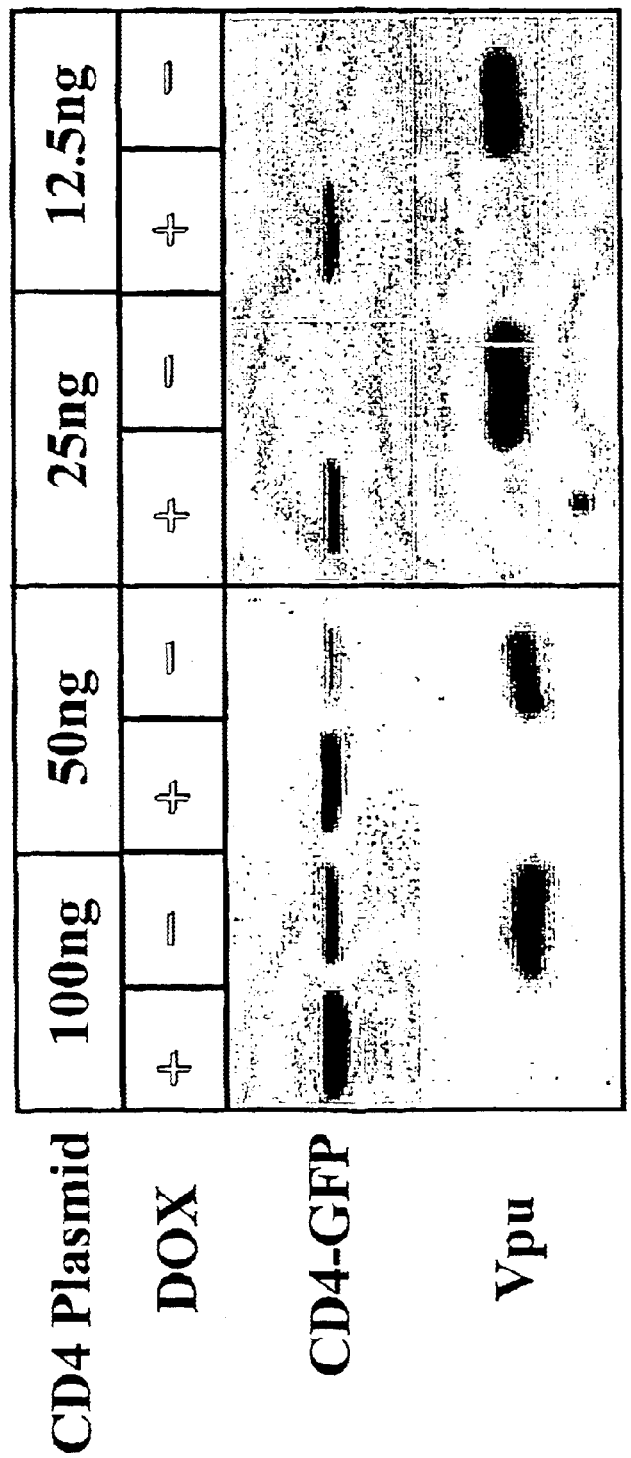
Figure 7C:
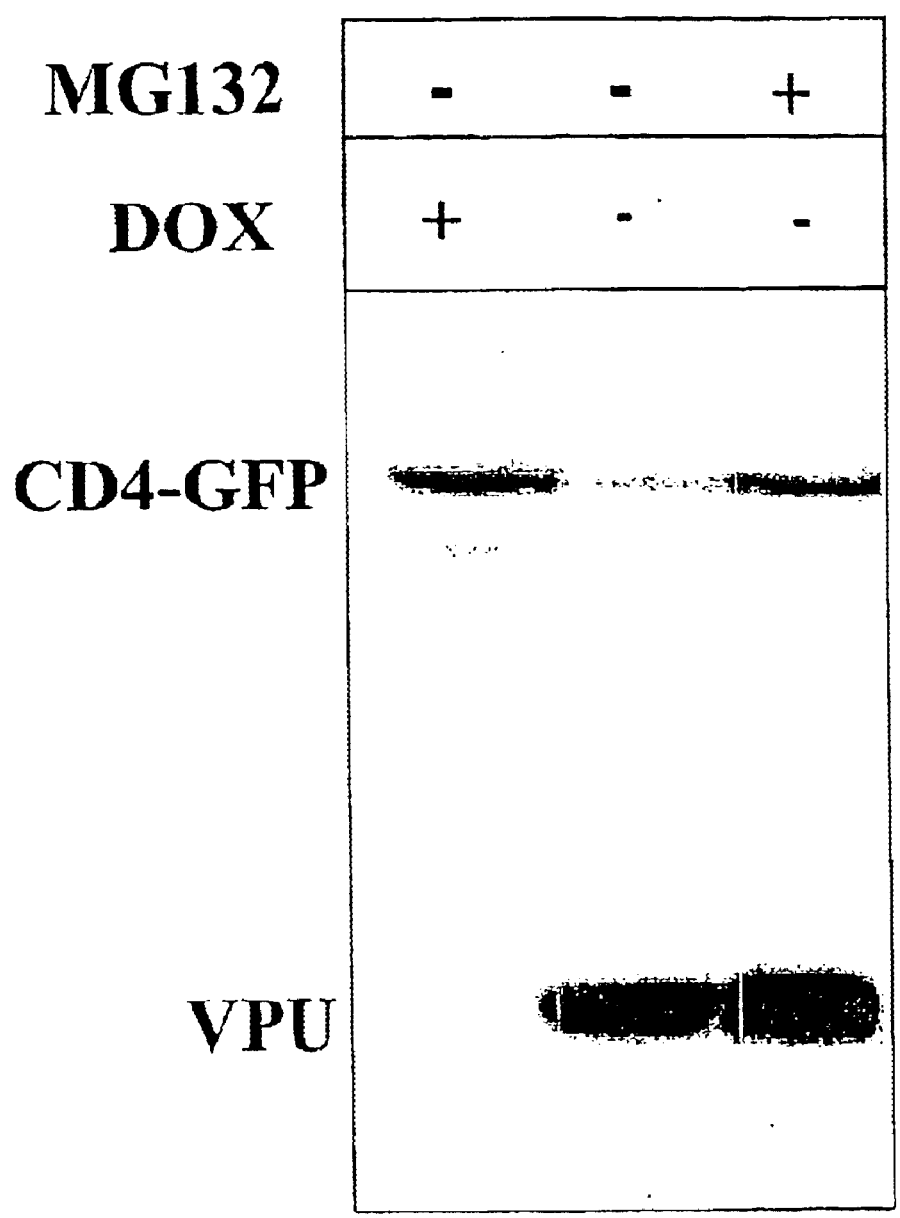

A GFP-CD4 expression plasmid was co-transfected into 293 cells together with expression plasmids for doxycycline (DOX)-regulated HIV-Vpu and tTA (tetracycline transactivator) plasmid. Vpu and GFP-CD4 expression were detected by Western blotting. Vpu was only expressed in the absence of DOX ("tet-off" system). At all plasmid inputs, but particularly at low levels (transfection of 25 ng/6 cm dish) the GFP-CD4 signal disappeared upon Vpu expression (FIG. 7B). Pretreatment of the transfected cells with the proteasome inhibitor MG132 (Lee and Goldberg (1998), resulted in the preservation of the GFP-CD4 signal (FIG. 7C). These results indicate that the proteasomal degradation of GFP-CD4 was mediated by Vpu, a known substrate of the E3RS ubiquitin ligase (Margottin et al., 1998).

Therefore, blocking the activity of the E3RS-hnRNP-U ligase complex should have an effect similar to proteasomal inhibition.

EXAMPLE 9

Immunoprecipitation of E3RS with polyclonal, hnRNP-U-specific antiserum.

A GST fusion protein containing the carboxy-terminal half of the human hnRNP-U protein (amino-acids 406–806, contained in a BamH1-Bgl2 fragment of the human hnRNP-U) was prepared as follows: The fragment was inserted into the BamH1 site of a commercially available bacterial expression vector (PGEX1, Clontech). The fusion protein was purified from bacterial lysates using glutathione-agarose affinity chromatography and glutathione elution according to standard procedures. Rabbits were injected with the fusion protein in complete Freund's adjuvant and were bled following 3 boosts. The anti-hnRNP-U serum was used to immunoprecipitate Flag-E3RS protein from transfected 293 cells. The E3RS immunoprecipitation capacity of the polyclonal rabbit antiserum (assayed by Western blotting) was comparable to that of the 3G6 monoclonal antibody (see Example 4) and was specific, as no E3RS was precipitated with the pre-immune serum of the same rabbit. Precipitation of the endogenous hnRNP-U from the same transfected cells was verified with the 3G6 antibodies, using Western blotting.

EXAMPLE 10

Identification of the hnRNP-U fragment that is responsible for interaction with E3RS.

To determine which part of hnRNP-U interacts with E3RS, several hnRNP-U fragments were prepared and examined for E3RS binding in transfected cells (FIG. 8A). A 198 amino acid N-terminal fragment of hnRNP-U, composed of long acidic (33% Glu and Asp) and short glutamine-rich peptide segments (Kiledjian and Dreyfuss, 1992) was found to interact with E3RS similarly to the intact protein, or to a 400 aa N-terminal fragment (FIG. 8B). The reciprocal 600 amino acid C-terminal fragment, containing the RNA-binding region (Kiledjian and Dreyfuss, 1992), bound only trace E3RS levels. There are no obvious IκBα degradation signals [DS(PO$_4$)GXXS(PO$_4$)] within the N-terminal hnRNP-U interacting fragment. Hence, it appears that the interaction of hnRNP-U with E3RS is a charge-based interaction, rather than the phosphate-based interaction that characterizes E3RS association with pIκBα.

FIG. 8 shows the binding of E3RS to the acidic N-terminal domain of hnRNP-U.

(A) Schematic representation of hnRNP-U and its fragments: N, N-198 and C. Indicated are the positions of various structural segments of the molecules (Kiledjian and Dreyfuss, 1992). Underlined are the NLS lysine residues, which when substituted, compromise NLS function (see below). (B) 293 cells were transfected with Flag tagged hnRNP-U or its single fragments (as in A; marked in B with an asterisk), together with HA-E3RS. Cell lysates were prepared and immunoprecipitated using anti-Flag antibodies. Western blot analysis was performed using anti-Flag, HA and hnRNP-U antibodies. Of note is the slower migration of the N-terminal fragments running at a position corresponding to 1.5 times their predicted size, possibly due to a charge effect or a posttranslational modification at the N-terminal region.

EXAMPLE 11

The subcellular localization of E3RS is determined by hnRNP-U.

To find out if the observed interaction between E3RS and hnRNP-U is maintained in vivo, their subcellular localization was examined by confocal microscopy. Nuclear colocalization of the two molecules was observed upon co-expression of GFP-E3RS with Flag-hnRNP-U in 293 cells (9A). On the other hand, Flag-hnRNP-U did not colocalize with nuclear GFP-histone 2A (9B), demonstrating the specificity of colocalization. In investigating the possible role of hnRNP-U in the subcellular localization of E3RS, several hnRNP-U mutants were constructed and examined for their effect on the localization of GFP-E3RS in 293 cells. hnRNP-U carries a putative NLS motif at amino acid position 223–231 (Kiledjian and Dreyfuss, 1992). A two amino acid mutation (substitution of lysines 224 and 228 by alanine) within the NLS had no effect on the interaction of the mutant hnRNP-U (mNLS) with E3RS (not shown), but resulted in mislocalization of the mutant protein to the cytoplasm (FIG. 9C). Another way of enforcing the cytoplasmic localization of hnRNP-U is through appending a nuclear export signal (NES) to the protein. The appended Rev-1-derived NES is responsible for exporting nuclear proteins to the cytoplasm via the Crm1 transport system (Henderson and Eleftheriou, 2000). Coexpression of both mislocalized hnRNP-U proteins with GFP-E3RS in 293 cells, resulted in the relocalization of E3RS from the nucleus to the cytoplasm (FIGS. 9C,E). Singly transfected cells, expressing only GFP-E3RS retained the nuclear expression of E3RS, indicating that the driving force for expelling E3RS from the nucleus was its association with the mislocalized hnRNP-U. This effect is specific, since GFP-histone 2A localization was not affected by any of the hnRNP-U variants (FIGS. 9D,F).

Figure 9:
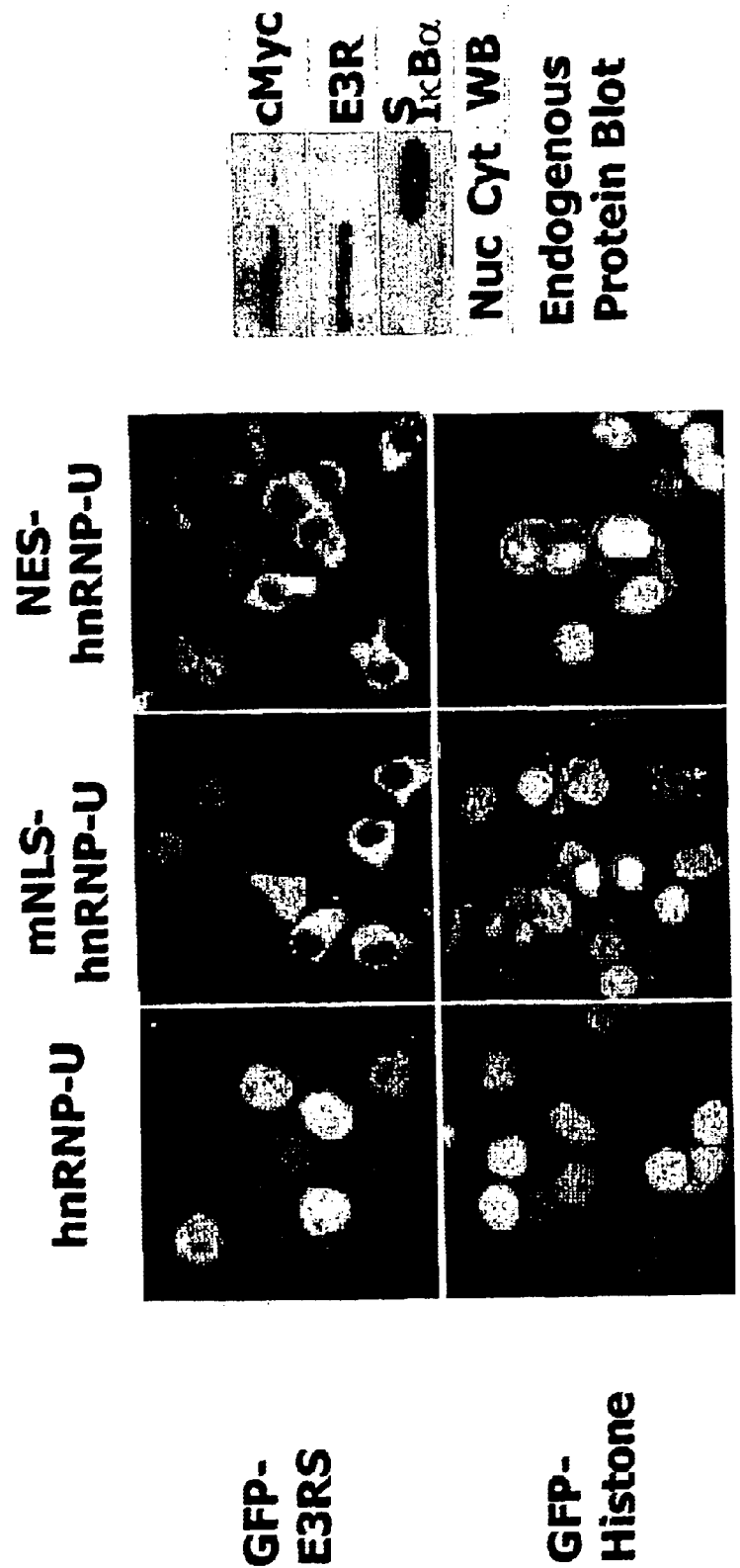
FIG. 9: Colocalization of E3RS with hnRNP-U in cell nuclei

FIG. 9 shows the colocalization of E3RS with hnRNP-U in cell nuclei.

(A) Western blot analysis of endogenous E3RS was performed with cytoplasmic and nuclear fractions of HeLa cells, using goat anti-β-TrCP/E3RS (C18, Santa Cruz). c-Myc and IκBα were used as references for the two cellular fractions. (B) Immunofluorescence studies. Left panels: 293 cells were transfected with Flag-WT-hnRNP-U (red) together with GFP-E3RS (green), or together with GFP-Histone 2A (green) and stained using anti-Flag and secondary Cy-5 conjugated antibodies. Middle Panel: Transfection with Flag-hnRNP-U-mNLS (red) together with GFP-E3RS or with GFP-Histone 2A. Right Panels: Transfection with Flag-NES-hnRNP-U (red) together with GFP-E3RS or GFP-Histone 2A.

EXAMPLE 12

Screening for modulators of E3RS activity by E3RS-hnRNP-U dissociation assay.

The assay is based on the intrinsic affinity of E3RS to the 198 aa N-terminal fragment of hnRNP-U (N-198, see Example 10) and the capacity of pIκBα-derived peptides or other compounds to induce E3RS-hnRNP-U dissociation. N-198 was fused to the N-terminus of bacterial alkaline phosphatase (AP) by genetic engineering in a manner that preserves the enzymatic activity of the fusion protein (Yamabahi and Kay, 2001). A pCDNA3-based expression vector encoding the fusion protein N198-AP was transfected into 293T cells together with a Flag-E3RS expression plasmid. Transfectants were lysed after 24–48 hrs and whole cell lysates were aliquoted onto a 384 well plate precoated with anti-Flag antibodies. Plates were washed several times with PBS-Tween 20 (0.1%) and were either used immediately for E3RS inhibitor screen or stored at 40 for a few days before use. All steps, including plate coating, washing and compound screen were automated. The position of the different compounds being tested for inducing the dissociation of N198-AP from E3RS was registered on computer for later reference. Compounds being tested for modulating activity were aliquoted (40 μL/well) into the test plates in duplicate. 20 μmol of the synthetic IκBαphosphopeptide pp10, or 200 μmol p10S/E (Example 3) were used as a positive or negative control, respectively. These peptide or miscellaneous compounds derived from combinatorial libraries were added to the plates, which were then agitated for 20 mins at room temperature. Following this incubation, 30 μL supernatants from each well were transferred onto a second plate containing 10 μL of the AP substrate pNPP in each well. The amount of N198-AP fusion protein in the supernatants was determined by pNPP hydrolysis measured by optical density (OD in an ELISA plate reader. OD values reflect the capacity of phosphopeptides or other compounds to modulate the E3RS binding activity for hnRNP-U (and by reference pIκBα, see Examples 3, 4).

TABLE 1

| Band number | Calculated molecular weight | Accession number | Gene name |
| --- | --- | --- | --- |
| 1 | 88946 | Q00839 (SwissProt) | HNRNPU |
| 2–4 | 68867 | Q9Y297 (trembl) | E3RS-IKAP |
| 5–6 | 31231 | Q04150 (trembl) | hnRNP C |
| 7–8 | 37429 | P22626 (trembl) | HNRPA2B1 |
| 9 | 38714 | P09651 (SwissProt) | HNRPA1 |
| 10 | 83264 | P08238 (SwissProt) | HSP90B |
| 11 | 70898 | P11142 (SwissProt) | HSPA8 |
| 12 | 70052 | P08107 (SwissProt) | HSPA1A |
| 13 | 60331 | P49368 (SwissProt) | CCT3 |
| 14 | 58024 | P40227 (SwissProt) | CCT6A |
|  | 59663 | P50990 (SwissProt) | CCT8 |
| 15 | 59220 | Q99832 (SwissProt) | CCT7 |
|  | 57624 | P50991 (SwissProt) | CCT4 |
| 16 | 48880 | CAA23844 (trembl) | BETA-TUBULIN |
| 17–18 | 68867 | Q9Y297 (trembl) | E3RS-IKAP |

REFERENCES

Alkalay, I., Yaron, A., Hatzubai, A., Orian, A., Ciechanover, A., and Ben-Neriah, Y. (1995). Stimulation-dependent IκBα phosphorylation marks the NF-κB inhibitor for degradation via the ubiquitin-proteasome pathway. Proc Natl Acad Sci USA 92, 10599–603.

Antisense Technology, Methods in Enzymology, 2000, ed. M. Ian Phillips, Academic Press Arenzana-Seisdedos, F., Turpin, P., Rodriguez, M., Thomas, D., Hay, R. T., Virelizier, J. L., and Dargemont, C. (1997). Nuclear localization of IκBα promotes active r of NF-kappa B from the nucleus to the cytoplasm. J Cell Sci 110, 369–78.

Bastiaens P I, Squire. Fluorescence lifetime imaging microscopy: spatial resolution of biochemical processes in the cell. Trends Cell Biol. 1999 February;9(2):48–52 Bai, C., Sen, P., Hofmann, K., Ma, L., Goebl, M., Harper, J. W., and Elledge, S. J. (1996). SKP1 connects cell cycle regulators to the ubiquitin proteolysis machinery through a novel motif, the F-box. Cell 86, 263–74.

Bosher, J. M. and Labouesse, M., (2000), Nat Cell Biol, February; 2(2):E31–6

Buchner, J. (1999). Hsp90 & Co.—a holding for folding. Trends Biochem Sci 24, 136–41.

Cohen, A. E., Tewillinger, E. F., Sodroski, J. G. and Hasseltine, W. A. (1988). Nature 334, 532–534

Cohen, N.C., et al., (1990). J. Med. Chem., 33:883–894

Current Protocols in Molecular Biology, Asubel et al., John Wiley and Sons, Inc.

Deshaies, R. J. (1999). SCF and Cullin/Ring H2-based ubiquitin ligases. Annu Rev Cell Dev Biol 15, 435–67.

Degterev A, Lugovskoy A, Cardone M, Mulley B, Wagner G, Mitchison T, Yuan J. Identification of small-molecule inhibitors of interaction between the BH3 domain and Bcl-xL. Nat Cell Biol. 2001, 3: 173–82

Dunican D J and Doherty P. (Designing cell-permeant phosphopeptides to modulate intracellular signaling pathways. Biopolymers 60:45–60, 2001)

Dreyfuss, G., Choi, Y. D., and Adam, S. A. (1984). Characterization of heterogeneous nuclear RNA-protein complexes in vivo with monoclonal antibodies. Mol Cell Biol 4, 1104–14.

Estes, -S-D; Stoler, -D-L and Anderson, -G-R. Normal fibroblasts induce the C/EBP beta and ATF-4 bZIP transcription factors in response to anoxia. Exp-Cell-Res. 220: 47–54, 1995

Fang, G., Yu, H., and Kirschner, M. W. (1998). Direct binding of CDC20 protein family members activates the anaphase-promoting complex in mitosis and GI. Mol Cell 2, 163–71.

Farmer, P. S., (1980), Drug Design, Ariens, E. J, ed., Vol. 10, pp. 119–143 (Academic Press, New York) Feldman, D. E., Thulasiraman, V., Ferreyra, R. G., and Frydman, J. (1999). Formation of the VHL-elongin BC tumor suppressor complex is mediated by the chaperonin TRiC. Mol Cell 4, 1051–461.

Feldman, R. M. R., Correll, C. C., Kaplan, K. B., and Deshaies, R. J. (1997). A complex of Cdc4p, Skp1p, and Cdc53p/cullin catalyzes ubiquitination of the phosphorylated CDK inhibitor Siclp. Cell 91, 221–230.

Feriasamy A, Day RN. Visualizing protein interactions in living cells using digitized GFP imaging and FRET microscopy. Methods Cell Biol. 1999;58:293–314.

Fire, A., Xu, S., Montgomery, M. K., Kostas, S. A., Driver, S. E., and Mello, C. C. (1998). Potent and specific genetic interference by double-stranded RNA in Caenorhabditis elegans. Nature 391, 806–11.

Fire, A., (1999), Trends Genet, Sep; 15(9):358–63

Fuchs, S. Y., Chen, A., Xiong, Y., Pan, Z. Q., and Ronai, Z. (1999). HOS, a human homolog of Slimb, forms an SCF complex with Skp1 and Cullin1 and targets the phosphorylation-dependent degradation of IκB and beta-catenin. Oncogene 18, 2039–46.

Ghosh S, May M J, Kopp E B. NF-kappa B and Rel proteins: evolutionarily conserved mediators of immune responses. Annu Rev Immunol. 1998;16:225–60. Gohring, F., Schwab, B. L., Nicotera, P., Leist, M., and Fackelmayer, F. 0. (1997). The novel SAR-binding domain of scaffold attachment factor A (SAF-A) is a target in apoptotic nuclear breakdown. Embo J 16, 7361–71.

Goss, -K-H and Groden, -J. Biology of the adenomatous polyposis coli tumor suppressor. J-Clin-Oncol. 18: 1967–79, 2000)

Gossen and Bujard, (1992). Proc Natl Acad Sci USA Jun 15;89(12):5547–51

Gurtu V, Yan G, Zhang G. IRES bicistronic expression vectors for efficient creation of stable mammalian cell lines. Biochem Biophys Res Commun. 1996. 229:295–8

Hanson, R. D., and Ley, T. J. (1992). A-T-rich scaffold attachment regions flank the hematopoietic serine protease genes clustered on chromosome 14q11.2. Blood 79, 610–8.

Hatakeyama, S., Kitagawa, M., Nakayama, K., Shirane, M., Matsumoto, M., Hattori, K., Higashi, H., Nakano, H., Okumura, K., Onoe, K., Good, R. A., and Nakayama, K. (1999). Ubiquitin-dependent degradation of IκBα is mediated by a ubiquitin ligase Skp1/Cul 1/F-box protein FWD1. Proc Natl Acad Sci USA 96, 3859–63.

Hattori K. et al., (1999), J. Biol. Chem. 274; 2964–29647

Henderson, B. R. & Eleftheriou, A. A comparison of the activity, sequence specificity, and CRM1-dependence of different nuclear export signals: *Exp Cell Res* 256: 213–24. (2000)

Hershko, A., and Ciechanover, A. (1998). The ubiquitin system. Annu. Rev. Biochem. 67, 425–479.

Huxford, T., Huang, D. B., Malek, S., and Ghosh, G. (1998). The crystal structure of the IκBα/NF-κB complex reveals mechanisms of NF-κB inactivation. Cell 95, 759–770.

Jacobs, M. D., and Harrison, S. C. (1998). Structure of an IκBα/NF-κB complex. Cell 95, 749–758.

Johnson, C., Van Antwerp, D., and Hope, T. J. (1999). An N-terminal nuclear export signal is required for the nucleocytoplasmic shuttling of IκBα. Embo J 18, 6682–93.

Karin, M., and Ben-Neriah, Y. (2000). Phosphorylation meets ubiquitination: the control of NF-κB activity. Annu Rev Immunol 18, 621–63.

Kieber-Emmons T, Murali R and Greene MI. (Therapeutic peptides and peptidomimetics. Curr Opin Biotechnol. 8:435–41, 1997)

Kiledjian, M., and Dreyfuss, G. (1992). Primary structure and binding activity of the hnRNP U protein: binding RNA through RGG box. Embo J 11, 2655–64.

Kim, M. K., and Nikodem, V. M. (1999). hnRNP U inhibits carboxy-terminal domain phosphorylation by TFIIH and represses RNA polymerase II elongation. Mol Cell Biol 19, 6833–44.

Kobinger, G. P., Mouland, A. J., Lalonde, J-P., Forget, J and Choen, E. A. (1997). Gene Therapy 4, 868–874.

Köhler and Milstein, 1975, Nature 265:495

Krecic, A. M., and Swanson, M. S. (1999). hnRNP complexes: composition, structure, and function. Curr Opin Cell Biol 11, 363–71.

Krek, W. (1998). Proteolysis and the G1-S transition: the SCF connection. Curr Opin Genet Dev 8, 36–42.

Kuntz, I. D., (1992), Science 257:1078–1082

Lama, J., Mangasarian, A., and Trono, D. (1999). Cell-surface expression of CD4 reduces HIV-1 infectivity by blocking Env incorporation in a Nef- and Vpu-inhibitable manner. Curr Biol 9, 622–31

Lambright, D. G., Sondek, J., Bohm, A., Skiba, N. P., Hamm, H. E., and Sigler, P. B. (1996). The 2.0 A crystal structure of a heterotrimeric G protein. Nature 3 79, 311–9.

Lassot, -I; Segeral, -E; Berlioz-Torrent, -C; Durand, -H; Groussin, -L; Hai, -T; Benarous, -R; Margottin-Goguet, -F. ATF4 degradation relies on a phosphorylation-dependent interaction with the SCF(betaTrCP) ubiquitin ligase. Mol-Cell-Biol. 21: 2192–202, 2001).

Lavon et al., (2000), Nat Med 2000 May;6(5):573–7

Lee, F. S., Peters, R. T., Dang, L. C., and Maniatis, T. (1998). MEKK1 activates both IκB kinase α and IκB kinase β. Proc. Natl. Acad. Sci.USA 95, 9319–9324.

Lee D H, Goldberg A. L. Proteasome inhibitors: valuable new tools for cell biologists. Trends Cell Biol. 1998 8:397–403)

Lenburg, M. E and Landau, N. R. (1993). J.Virol. 67, 7238–7245.

Lewis AJ, Manning AM. New targets for anti-inflammatory drugs. Curr Opin Chem Biol. 1999 3:489–94.

Louvion, J. F., Warth, R., and Picard, D. (1996). Two eukaryote-specific regions of Hsp82 are dispensable for its viability and signal transduction functions in yeast. Proc Natl Acad Sci USA 93, 13937–42.

Lyapina, S. A., Correll, C. C., Kipreos, E. T., and Deshaies, R. J. (1998). Human CUL1 forms an evolutionarily conserved ubiquitin ligase complex (SCF) with SKP1 and an F-box protein. Proc Natl Acad Sci USA 95, 7451–6.

Maddon, P. J., Littman, M. G., Godfrey, M., Maddon, D. E., Chess, L and Axel, R. (1985). Cell 42, 93–104.

Maniatis, T. (1999). A ubiquitin ligase complex essential for the NF-κB, Wnt/Wingless, and Hedgehog signaling pathways. Genes and Development 13, 505–10.

Margottin, F., Bour, S. P., Durand, H., Selig, L., Benichou, S., Richard, V., Thomas, D., Strebel, K., and Benarous, R. (1998). A novel human WD protein, h-beta TrCP, that interacts with HIV-1 Vpu connects CD4 to the ER degradation pathway through an F-box motif. Mol Cell 1, 565–574.

Marx J. Why some leukemia cells resist STI-571. Science. 292 :2231–3 (2001)

Mayo M W, Baldwin AS. 2000, The transcription factor NF-κB: control of oncogenesis and cancer therapy resistance. Biochim Biophys Acta. 1470:M55–62.

Mercurio, F., Zhu, H., Murray, B. W., Shevchenko, A., Bennett, B. L., Li, J., Young, D. B., Barbosa, M., Mann, M., Manning, A., and Rao, A. (1997). IKK-1 and IKK-2: cytokine-activated IκB kinases essential for NF-κB activation. Science 278, 860–866.

Mercurio F, Manning AM. 1999, NF-kappaB as a primary regulator of the stress response. Oncogene.,18:6163–71.

Morishima, Y., Murphy, P. J., Li, D. P., Sanchez, E. R., and Pratt, W. B. (2000). Stepwise assembly of a glucocorticoid receptor.hsp90 heterocomplex resolves two sequential ATP-dependent events involving first hsp70 and then hsp90 in opening of the steroid binding pocket. J Biol Chem.

Nakielny, S., and Dreyfuss, G. (1999). Transport of proteins and RNAs in and out of the nucleus. Cell 99, 677–90.

Nathan, D. F., Vos, M. H., and Lindquist, S. (1997). In vivo functions of the Saccharomyces cerevisiae Hsp90 chaperone. Proc Natl Acad Sci USA 94, 12949–56.

Navia, M. A. and Murcko, M. A., (1992), Current Opin in Structural Biol, 2:202–210.

Ohta, T., Michel, J. J., Schottelius, A. J., and Xiong, Y. (1999). ROC1, a homolog of APC11, represents a family of cullin partners with an associated ubiquitin ligase activity. Mol Cell 3, 535–41.

Patton, E. E., Willems, A. R., and Tyers, M. (1998). Combinatorial control in ubiquitin-dependent proteolysis: don't Skp the F-box hypothesis. Trends Genet 14, 236–243.

Picard, D., Khursheed, B., Garabedian, M. J., Fortin, M. G., Lindquist, S., and Yamamoto, K. R. (1990). Reduced levels of hsp90 compromise steroid receptor action in vivo. Nature 348, 166–8.

Pinol-Roma, S., Choi, Y. D., Matunis, M. J., and Dreyfuss, G. (1988). Immunopurification of heterogeneous nuclear ribonucleoprotein particles reveals an assortment of RNA-binding proteins. Genes Dev 2, 215–27.

Polakis, P. (1999). The oncogenic activation of beta-catenin. Curr Opin Genet Dev 9, 15–21.

Pollok B A, Heim R. (1999) Using GFP in FRET-based applications. Trends Cell Biol. February; 9(2):57–60

Ratner, L. et al. (1985), Nature 313, 277–283

Remington Pharmaceutical Sciences, 1995, Remington: the science and practice of pharmacy. 19th ed., Mack Publ. Co., Easton, Pa., Osol (ed.).

Renard, P., Percherancier, Y., Kroll, M., Thomas, D., Virelizier, J. L., Arenzana-Seisdedos, F., and Bachelerie, F. (2000). Inducible NF-KB Activation Is Permitted by Simultaneous Degradation of Nuclear IκBα. J Biol Chem 275, 15193–15199.

Romig, H., Fackelmayer, F. O., Renz, A., Ramsperger, U., and Richter, A. (1992). Characterization of SAF-A, a novel nuclear DNA binding protein from HeLa cells with high affinity for nuclear matrix/scaffold attachment DNA elements. Embo J 11, 3431–40.

Rosser, M. F. N. and Nichitta, C. V. (2000), J. Biol. Chem. 275; 22798–22805 Sadot, E., Simcha, I., Iwai, K., Ciechanover, A., Geiger, B., and Ben-Ze'ev, A. (2000). Differential interaction of plakoglobin and beta-catenin with the ubiquitin-proteasome system. Oncogene 19, 1992–2001.

Seol, J. H., Feldman, R. M., Zachariae, W., Shevchenko, A., Correll, C. C., Lyapina, S., Chi, Y., Galova, M., Claypool, J., Sandmeyer, S., Nasmyth, K., and Deshaies, R. J. (1999). Cdc53/cullin and the essential Hrt1 RING-H2 subunit of SCF define a ubiquitin ligase module that activates the E2 enzyme Cdc34. Genes Dev 13, 1614–1626.

Sharp, P.A., (1999), Genes Dev, January 15; 13(2):139–41

Shevchenko, A., Wilm, M., Vorm, O., Jensen, 0. N., Podtelejnikov, A. V., Neubauer, G., Mortensen, P., and Mann, M. (1996). A strategy for identifying gel-separated proteins in sequence databases by MS alone. Biochem Soc Trans 24, 893–6.

Shin, J., Dunback, R. L, Lee, S. and Strominger, J. L. (1991). Proc. Natl. Acad. Sci. USA. 88, 1918–1922.

Skowyra, D., Craig, K. L., Tyers, M., Elledge, S. J., and Harper, J. W. (1997). F-box proteins are receptors that recruit phosphorylated substrates to the SCF ubiquitin-ligase complex. Cell 91, 209–19.

Skowyra, D., Koepp, D. M., Kamura, T., Conrad, M. N., Conaway, R. C., Conaway, J. W., Elledge, S. J., and Harper, J. W. (1999). Reconstitution of G1 cyclin ubiquitination with complexes containing SCFGrr1 and Rbx1. Science 284, 662–5.

Smith, D. F., Whitesell, L., and Katsanis, E. (1998). Molecular chaperones: biology and prospects for pharmacological intervention. Pharmacol Rev 50, 493–514.

Sondek, J., Bohm, A., Lambright, D. G., Hamm, H. E., and Sigler, P. B. (1996). Crystal structure of a G-protein beta gamma dimer at 2.1A resolution. Nature 379, 369–74.

Suzuki, H., Chiba, T., Suzuki, T., Fujita, T., Ikenoue, T., Omata, M., Furuichi, K., Shikama, H., and Tanaka, K. (2000). Homodimer of two F-box proteins β-TRCP1 or β-TrCP2 binds to IκBα for signal-dependent ubiquitination. J Biol Chem 275, 2877–84.

Tan, P., Fuchs, S. Y., Chen, A., Wu, K., Gomez, C., Ronai, Z., and Pan, Z. Q. (1999). Recruitment of a ROC1-CUL1 ubiquitin ligase by Skp1 and HOS to catalyze the ubiquitination of IκBα. Mol Cell 3, 527–33.

Terwilliger, et al., (1989), Proc Natl Acad Sci USA July; 86(13):5163–7

Turpin, P., Hay, R. T., and Dargemont, C. (1999). Characterization of IκBα nuclear import pathway. J Biol Chem 274, 6804–12.

Varshavsky, A. (1997). The ubiquitin system. Trends Biochem Sci 22, 383–7.

Verlinde, C., (1994), Structure, 2:577–587

Vincent, M. J., Raja., N. U and Jabbar, M. A. (1993). J. Virol. 67, 5538–5549.

Wilm, M., Shevchenko, A., Houthaeve, T., Breit, S., Schweigerer, L., Fotsis, T., and Mann, M. (1996). Femtomole sequencing of proteins from polyacrylamide gels by nano-electrospray mass spectrometry. Nature 379, 466–469.

Winston, J. T., Strack, P., Beer-Romero, P., Chu, C. Y., Elledge, S. J., and Harper, J. W. (1999). The SCF β-TRCP-ubiquitin ligase complex associates specifically with phosphorylated destruction motifs in IκBα and β-catenin and stimulates IκBα ubiquitination in vitro. Genes Dev 13, 270–283.

Wu, G., Chen, Y. G., Ozdamar, B., Gyuricza, C. A., Chong, P. A., Wrana, J. L., Massague, J., and Shi, Y. (2000). Structural basis of Smad2 recognition by the Smad anchor for receptor activation. Science 287, 92–7.

Yamabahi M. and Kay B. K. (2001). Mapping protein-protein interactions with alkaline phosphatase fusion proteins. Methods in Enzymology 332: 88–102.

Yamano, H., Tsurumi, C., Gannon, J., and Hunt, T. (1998). The role of the destruction box and its neighbouring lysine residues in cyclin B for anaphase ubiquitin-dependent proteolysis in fission yeast: defining the D-box receptor. Embo J 17, 5670–8.

Yaron, A., Gonen, H., Alkalay, I., Hatzubai, A., Jung, S., Beyth, S., Mercurio, F., Manning, A. M., Ciechanover, A., and Ben-Neriah, Y. (1997). Inhibition of NF-κB cellular function via specific targeting of the IκB-ubiquitin ligase. EMBO J 16, 6486–6494.

Yaron, A., Hatzubai, A., Davis, M., Lavon, I., Amit, S., Manning, A. M., Andersen, J. S., Mann, M., Mercurio, F., and Ben-Neriah, Y. (1998). Identification of the receptor component of the IκBα-ubiquitin ligase. Nature 396, 590–594.

Yin, M. J., Christerson, L. B., Yamamoto, Y., Kwak, Y. T., Xu, S., Mercurio, F., Barbosa, M., Cobb, M. H., and Gaynor, R. B. (1998). HTLV-1 Tax protein binds to MEKK1 to stimulate IκB kinase activity and NF-κB activation. Cell 93, 875–884.

Zachariae, W., and Nasmyth, K. (1999). Whose end is destruction: cell division and the anaphase-promoting complex. Genes Dev 13, 2039–58.

Zachariae, W., Schwab, M., Nasmyth, K., and Seufert, W. (1998). Control of cyclin ubiquitination by CDK-regulated binding of Hct1 to the anaphase promoting complex. Science 282, 1721–4.

---

What is claimed is:

1. A method for identifying a compound that modulates, ubiquitin-mediated proteolysis of phosphorylated IκB, wherein the compound is tested for its capacity to directly or indirectly modulate, the ability of β-TrCP/E3RS to engage in protein-protein association with hnRNP-U.

2. The method of claim 1, wherein the compound is tested for its ability to disrupt the complex of the two interacting proteins β-TrCP/E3RS and hnRNP-U.

3. The method of claim 2, comprising the steps of
   a) incubating a complex containing the interacting proteins hnRNP-U and β-TrCP/E3RS or the protein domains required for their interaction, one of them being labeled by a detectable marker, with the test compound for a period of time sufficient to disrupt the complex, collecting aliquots of the dissociated protein that carries the detectable marker and b) monitoring the interaction of the proteins by measuring the signal generated by the release of the labeled protein and c) correlating the intensity of the signal generated by the release of the labeled protein and optionally the rate of signal emission with the ability of the test compound to disrupt the hnRNP-U/E3RS complex.

4. The method of claim 3, wherein in step b) the released protein is an enzyme fusion protein and the signal is generated through enzymatic reaction.

5. The method of claim 3, wherein the complex contains Skp1 in addition to the interacting proteins hnRNP-U and β-TrCP/E3RS.

6. The method of claim 3, wherein the complex contains the 198 amino acid N-terminal fragment of hnRNP-U, instead of hnRNP-U.

7. The method of claim 3, wherein a complex is used that has been obtained by stoichiometric co-expression of the proteins.

8. The method of any one of claim 3, wherein the detectable marker is selected from radioactive labels, fluorescent markers and enzymes.

9. The method of claim 8, wherein the fluorescent marker is Green Fluorescent Protein.

10. The method of claim 3, wherein the non-labeled interacting protein is immobilized onto a solid support.

11. The method of claim 10, wherein the protein is immobilized onto the support via the binding of an antibody and a tag.

12. The method of claim 3, wherein the interaction of the proteins is monitored by fluorescence measurement in solution.

13. The method of claim 12, wherein the interaction is monitored by Fluorescence Resonance Energy Transfer.

14. The method of claim 3, wherein an agent that is known to disrupt the complex is used as a positive control.

15. The method of claim 14, wherein the control agent contains the IκBα degradation motif.

16. The method of claim 15, wherein the control agent is phosphorylated IκBα or a synthetic IκBα phosphopeptide.

17. The method of claim 1, wherein the compound is tested for its ability to inactivate the hnRNP-U protein.

18. The method of claim 17, wherein the compound is tested for its ability to inhibit dissociation of hnRNP-U from β-TrCP/E3RS by a) incubating hnRNP-U, or a protein mixture containing hnRNP-U, with the test compound, b) incubating the hnRNP-U containing composition with labeled β-TrCP/E3RS and, optionally Skp1, for a period of time sufficient for the formation of a hnRNP-U/E3RS complex, c) monitoring the dissociation of the complex by incubating it with an agent known to induce the dissociation of the partner proteins and measuring the signal generated by the release of the labeled protein and d) correlating a reduction of the signal generated by the release of the labeled protein and optionally the rate of said reduction with the compound's hnRNP-U inactivating effect.

19. The method of claim 2, wherein the method comprises the steps of a) incubating mammalian cells that express the interacting proteins hnRNP-U and β-TrCP/E3RS, and optionally Skp1, one of the interacting proteins being labeled by fusion to a detectable marker protein, with the test compound for a period of time sufficient for the compound to penetrate the cell and disrupt the hnRNP-U/E3RS complex.

b) immunoprecipitating the cells with an antibody against the non-labeled protein, c) monitoring the co-precipitation of the labeled protein by measuring the generated signal, and d) correlating the absence or the reduction of the signal with the ability of the compound to disrupt the complex.

20. The method of claim 19, wherein the labeled protein is β-TrCP/E3RS and the antibody is an anti-hnRNP-U antibody.

21. The method of claim 19, wherein the marker protein is the Green Fluorescent Protein.

22. The method of claim 2, comprising a) incubating mammalian cells that express the interacting proteins hnRNP-U and β-TrCP/E3RS, or the protein domains required for their interaction, respectively, and optionally Skp1, the interacting proteins being labeled by different fluorescent marker proteins, with the test compound for a period of time sufficient for the compound to penetrate the cell and disrupt the hnRNP-U/E3RS complex, b) monitoring the interaction of the proteins by real-time measurement of a Fluorescence Resonance Energy Transfer signal, and c) correlating a decrease in the signal with the ability of the compound to disrupt the complex.

23. The method of claim 22, wherein the cells are transfected with two plasmids, each of them encoding one of the interacting proteins fused to a fluorescent protein.

24. The method of claim 23, wherein the fluorescent proteins are Yellow Fluorescent Protein (YFP) and Cyan Fluorescent Protein (CFP).

25. The method of claim 19, wherein steps a) and b) are performed in the presence of an agent that is known to induce dissociation of the hnRNP-U/E3RS complex, and the compound's ability to inactivate hnRNP-U is determined by detecting non-associated hnRNP-U with an anti-hnRNP-U antibody.

26. The method of claim 1, wherein the compound's capacity to interfere with the ability of β-TrCP/E3RS to engage in protein-protein association involving hnRNP-U is identified by determining its capacity of inhibiting HIV Vpu-dependent CD4 degradation.

27. The method of claim 26, wherein a mammalian cell line that reports CD4 degradation upon induction of Vpu expression, the reporter system comprising CD4 linked to a detectable label that produces a signal as long as CD4 is stably expressed, is incubated with the test compound and the compound's capacity of stabilizing the signal is correlated with its capacity of inhibiting HIV Vpu-dependent CD4 degradation.

28. The method of claim 27, comprising a) transfecting mammalian cells with i) a CD4 plasmid that carries a human CD4 sequence fused to a label in the form of a marker protein sequence, the CD4 sequence being truncated at its C-terminus down to the ER retention signal, the N-terminal CD4 sequence including the first three Ig-like domains, under preservation of the CD4 signal sequence, being replaced with the marker sequence, and ii) a plasmid containing the HIV Vpu sequence under the control of a regulatable promoter such that Vpu is only produced in the absence of an expression modifier, b) growing the cells in the presence of said expression modifier under conditions that prevent Vpu expression and CD4 degradation, allowing CD4 to produce a detectable signal, c) growing the cells in the absence of said expression modifier under conditions that allow Vpu expression and CD4 degradation, preventing CD4 to produce a detectable signal, d) incubating the cells with the test compound and further growing them in the absence of the expression modifier, thereby causing Vpu expression and CD4 degradation, e) monitoring the signal generated by CD4 and f) correlating the signal generated upon stabilization of CD4 with the ability of the test compound to inhibit Vpu-dependent CD4 degradation.

29. The method of claim 27, comprising the steps a) transfecting mammalian cells with
i) a CD4 plasmid that carries a human CD4 sequence fused to a label in the form of a marker protein sequence, the CD4 sequence being truncated at its C-terminus down to the ER retention signal, the N-terminal CD4 sequence including he first three Ig-like domains, under preservation of the CD4 signal sequence, being replaced with the marker sequence, and
ii) a plasmid containing the HI Vpu sequence under the control of a regulatable promoter such that Vpu is only produced in the absence of an expression modifier, b) monitoring the signal generated by CD4;

c) correlating the signal generated upon stabilization of CD4 with the ability of the test compound to inhibit Vpu-dependent CD4 degradation;

d) growing the cells in the absence of the said expression modifier under conditions that prevent Vpu expression and CD4 degradation, allowing CD4 to produce a detectable signal, e) growing the cells in the presence of said expression modifier under conditions that allow Vpu expression and CD4 degradation, preventing CD4 to produce a detectable signal, and f) incubating the cells with the test compound and further growing them in the presence of the expression modifier, thereby causing continued Vpu expression and CD4 degradation.

30. The method of claim 27, wherein the CD4 marker is a fluorescent protein.

31. The method of claim 30, wherein the fluorescent protein is the Green Fluorescent Protein.

32. The method of claim 27, wherein the CD4 marker is an enzyme.

33. The method of claim 32, wherein the enzyme is luciferase.

34. The method of claim 27, wherein Vpu expression is regulated by the tetracycline promoter and wherein the expression modifier is doxycycline.

35. The method of claim 27, wherein a proteasome inhibitor is used as a positive control.

36. A pharmaceutical composition, containing as active ingredient an NF-κB inhibitory compound which has the capacity to interfere, directly or indirectly, with the ability of β-TrCP/E3RS to engage in protein-protein associated with hnRNP-U.

37. The pharmaceutical composition of claim 36, further comprising a second NF-κB inhibitory compound that inhibits NF-κB activation by a different mechanism.

38. The pharmaceutical composition of claim 37, wherein said second NF-κB inhibitory compound is an IκB-kinase (IKK) inhibitor.

39. An NF-κB inhibitory compound, characterized in that said compound is a peptide derived from the amino acid sequence of hnRNP-U.

40. A peptide of claim 39 with the amino acid sequence as set forth in SEQ ID NO: 1.

41. A peptide of claim 39 with the amino acid sequence as set forth in SEQ ID NO:2.

42. A peptide of claim 39 with the amino acid sequence as set forth in SEQ ID NO:3.

43. A peptide of claim 39 with the amino acid sequence as set forth in SEQ ID NO:4.

44. An NF-κB inhibitory compound, characterized in that said compound is an oligonucleotide derived from the nucleotide sequence of hnRNP-U.

45. An NF-κB inhibitory oligonucleotide of claim 44 encoding a peptide with the amino acid sequence as set forth in SEQ ID NO:1, 2, 3 or 4.

46. A pharmaceutical composition comprising as an active ingredient a compound that has the capacity to interfere directly or indirectly, with the ability of β-TrCP/E3RS to engage in protein-protein association with hnRNP-U, wherein the compound is obtainable by rational design based on the crystal structure of a complex containing β-TrCP/E3RS and hnRNP-U, and optionally Skp1.

47. The pharmaceutical composition to claim 46, wherein the complex is obtained by co-crystallization of the complex constituents.

48. Isolated E3RS precipitating anti hnRNP-U antibodies for the diagnosis of conditions in which the β-TrCP/E3RS is compromised.

49. Isolated IκB precipitating anti hnRNP-U antibodies for monitoring the therapeutic efficacy of an inhibitor of ubiquitin-mediated proteolysis of phosphorylated IκB.

50. A method for producing a functional β-TrCP/E3RS, comprising co-expressing β-TrCP/E3RS and hnRNP-U optionally together with Skp1, in a bacterial, yeast or insect cell.

51. The pharmaceutical composition of claim 37, wherein said second NF-κB inhibitory compound inhabits NF-κB activation by a mechanism not involving association of B-TrCP/E2RS with hnRNP-U.

52. The pharmaceutical composition of claim 37, for the treatment of cancer, by preventing the emerging of resistant tumor cells.

53. The method of claim 1, for identifying a compound that inhibits ubiquitin-mediated proteolysis of phosphorylated IκB, wherein said compound competes or interferes with the ability of βTrCP/E3RS to engage in protein-protein association with hnRNP-U.

54. A pharmaceutical composition containing as active ingredient a compound that inactivates hnRNP-U protein wherein the compound has the capacity to interfere, directly or indirectly, with the ability of β-TrCP/E3RS to engage in protein-protein association with hnRNP-U.

* * * * *

UNITED STATES PATENT AND TRADEMARK OFFICE
CERTIFICATE OF CORRECTION

PATENT NO. : 6,905,836 B2  Page 1 of 1
DATED : June 14, 2005
INVENTOR(S) : Yinon Ben-Neriah et al.

It is certified that error appears in the above-identified patent and that said Letters Patent is hereby corrected as shown below:

Column 34,
Line 66, change "andß-TrCP/E3RS" to -- and ß-TrCP/E3RS --.

Column 35,
Line 23, delete "of any one".

Column 37,
Line 28, change "he" to -- the --.
Line 32, change "HI Vpu" to -- HIV Vpu --.

Column 38,
Line 14, change "NO: 1" to -- NO:1 --.
Line 50, change "inhabits" to -- inhibits --.

Signed and Sealed this

Twenty-third Day of August, 2005

JON W. DUDAS
*Director of the United States Patent and Trademark Office*